United States Patent
Desobry et al.

(10) Patent No.: US 6,576,684 B1
(45) Date of Patent: Jun. 10, 2003

(54) THERMAL- AND PHOTOINITIATED RADICAL POLYMERIZATION IN THE PRESENCE OF AN ADDITION FRAGMENTATION AGENT

(75) Inventors: Vincent Desobry, Marly (CH); Peter Murer, Allschwil (CH); Anne Schuwey, Arconciel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/763,015

(22) PCT Filed: Aug. 10, 1999

(86) PCT No.: PCT/EP99/05789

§ 371 (c)(1),
(2), (4) Date: Feb. 15, 2001

(87) PCT Pub. No.: WO00/11041

PCT Pub. Date: Mar. 2, 2000

(30) Foreign Application Priority Data

Aug. 21, 1998 (EP) .............................. 98810820

(51) Int. Cl.$^7$ ...................... C08F 2/50; C07C 255/30; C07C 229/30; C07C 211/63; C07C 381/12; C07F 9/54; C07D 295/02

(52) U.S. Cl. ...................... 522/167; 522/171; 522/168; 522/173; 522/180; 522/182; 522/186; 522/188; 526/256; 526/258; 526/263; 526/274; 526/286; 526/310; 526/328; 526/328.5; 526/346; 526/347; 526/348; 526/348.8; 564/281; 564/291; 564/292; 564/296; 568/8; 568/13; 568/17; 568/18; 568/74; 568/75; 568/77

(58) Field of Search ................... 522/167, 171, 522/173, 180, 182, 186, 188, 168; 526/310, 256, 258, 263, 274, 286, 328, 328.5, 329.3, 346, 347, 348, 348.8; 564/281, 291, 292, 296; 568/8, 9, 11, 13, 16, 17, 18, 38, 39, 42, 43, 44, 45, 56, 74, 75

(56) References Cited

U.S. PATENT DOCUMENTS

| | | | | |
|---|---|---|---|---|
| 3,926,756 A | * | 12/1975 | Restaino | 522/173 |
| 5,459,007 A | * | 10/1995 | Larson et al. | 430/115 |
| 5,610,248 A | * | 3/1997 | Hogan-Esch et al. | 526/193 |
| 5,998,091 A | * | 12/1999 | Suzuki | 430/270.1 |
| 6,291,620 B1 | * | 9/2001 | Moad et al. | 526/319 |
| 6,399,731 B2 | * | 6/2002 | King et al. | 526/318.4 |

FOREIGN PATENT DOCUMENTS

| | | |
|---|---|---|
| DE | 4305332 | 9/1993 |
| EP | 0390439 | 10/1990 |
| GB | 1391806 | 4/1975 |
| WO | 88/04304 | 6/1988 |

OTHER PUBLICATIONS

J. Polymer Science: Part A: Polymer Chemistry, vol. 34, pp. 3621–3624 (1996).
D. Colombani et al., Prog. Polym. Sci., vol. 21, pp. 439–503, (1996).

* cited by examiner

Primary Examiner—Susan W. Berman
(74) Attorney, Agent, or Firm—Tyler A. Stevenson

(57) ABSTRACT

Disclosed are compositions from which radically initiated oligomers/polymers having a controlled molecular weight, low polydispersity and a vinyl or dienyl end group are prepared. Further subjects of the invention are a process for controlled radical polymerization, oligomers/polymers obtainable by said process and the use of specific addition fragmentation agents for the polymerization process. The addition fragmentation agents are new in part and these are also subject of the present invention. The addition fragmentation agents are of the formula (Ia), (Ib) or (Ic)

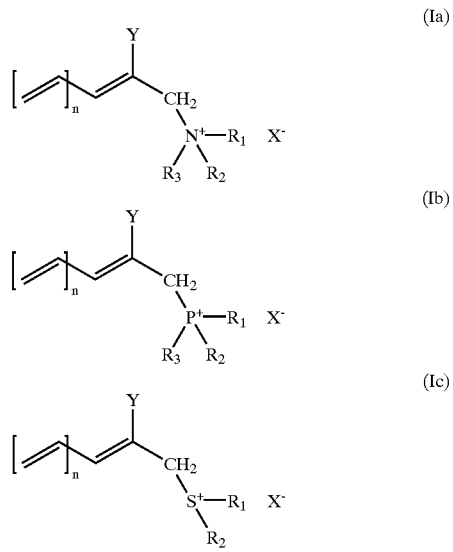

where Y is a group which activates the double bond towards Michael addition.

20 Claims, No Drawings

THERMAL- AND PHOTOINITIATED RADICAL POLYMERIZATION IN THE PRESENCE OF AN ADDITION FRAGMENTATION AGENT

The present invention relates to compositions, from which radically initiated oligomers/polymers having a controlled molecular weight, low polydispersity and a vinyl or dienyl end group can be prepared. Further subjects of the invention are a process for controlled radical polymerization, oligomers/polymers obtainable by said process and the use of specific addition fragmentation agents for the polymerization process. The addition fragmentation agents are new in part and these are also subject of the present invention.

Polymers of limited molecular weight, or oligomers, are useful as precursors in the manufacture of other polymeric materials and as additives in plastics, elastomers and surface coating compositions, as well as being useful in their own right in many applications.

In conventional polymerization practice, the manufacture of oligomers requires the use of an initiator which acts as free radical source and of a chain transfer agent. The chain transfer agent controls the molecular weight of the polymer molecule by reacting with the propagating polymer chain. At least a part of the transfer agent is incorporated into the polymer and thus is consumed during the process. The incorporated residue of the chain transfer agent can lead to undesirable end-groups on the polymer. Common chain transfer agents are for example alkanethiols, which cause an objectionable odour.

To avoid these deficiencies WO 88/04304 suggests non-ionic acrylate or styrene derivatives as chain transfer agents for controlled radical polymerization.

The use of addition fragmentation agents to control molecular weight is known and a variety of compounds have already been suggested as for example described by Colombani et al. in "Addition Fragmentation Processes in Free Radical Polymerization", Prog. Polym. Sci., Vol. 21, 439–503, 1996. However there is still a need to provide easily accessible compounds which are highly efficient in thermally and in photochemically induced radical polymerization.

Y. Yagci et al. in J. Polym. Sci., Part A, Polym. Chem. Vol. 34, 3621–3624 (1996) disclose the use of allyl onium salts, in particular pyridinium salts, together with radical initiators for cationic polymerization.

Surprisingly it has been found that specific allyl or dienyl cationic systems are highly efficient addition fragmentation agents, useful for the control of molecular weight build up of radical polymerizations. The chain transfer coefficient $c_x$ is in many cases close to the theoretically ideal value of 1. Polydispersity of the oligomers/polymers is generally small and in many cases below 2. The compounds are easily accessible thus being ideally suitable for industrial applications.

These polymerization processes will also control the physical properties of the resulting polymers such as viscosity, hardness, gel content, processability, clarity, high gloss, durability, and the like.

The polymerization processes and resin products of the present invention are useful in many applications, including a variety of specialty applications, such as for the preparation of block copolymers which are useful as compatibilizing agents for polymer blends, or dispersing agents for coating systems or for the preparation of narrow molecular weight resins or oligomers for use in coating technologies and thermoplastic films or as toner resins and liquid immersion development ink resins or ink additives used for electrophotographic imaging processes.

One object of the present invention is a composition comprising a) at least one ethylenically unsaturated monomer or oligomer b) at least one radical initiator which forms a radical upon heating or upon irradiation with (UV) light from 305 nm to 450 nm and c) a compound of formula (Ia), (Ib) or (Ic)

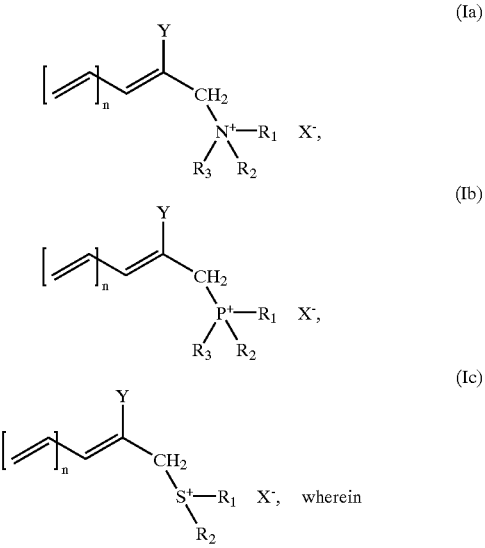

Y is a group which activates the double bond towards Michael addition;

X is halogen or the anion of a mono carboxylic acid from 1–12 carbon atoms, a monovalent oxo acid or complex acid;

n is 0 or 1;

$R_1$, $R_2$, $R_3$ are independently of each other hydrogen, unsubstituted $C_1$–$C_{18}$alkyl, $C_3$–$C_{18}$alkyl, interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl or $C_3$–$C_{18}$alkyl interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino, di($C_1$–$C_4$alkyl)amino or by a group —O—C(O)—$C_1$–$C_{18}$alkyl; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or $R_1$ and $R_2$, together with the linking hetero atom, form a $C_3$–$C_{12}$heterocycloalkyl radical; or $R_1$ and $R_2$ form a group,

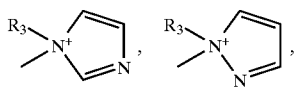

or $R_1$, $R_2$ and $R_3$ form a group

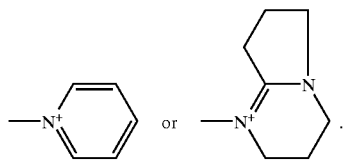

Halogen is fluorine, chlorine, bromine or iodine, preferably chlorine or bromine.

The alkyl radicals in the various substituents may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Alkenyl with 3 to 18 carbon atoms is a linear or branched radical as for example propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl oder n-4-octadecenyl. Preferred is alkenyl with 3 bis 12, particularly preferred with 3 to 6 carbon atoms.

Alkinyl with 3 to 18 is a linear or branched radical as for example propinyl (—CH$_2$—C≡CH), 2-butinyl, 3-butinyl, n-2-octinyl, oder n-2-octadecinyl. Preferred is alkinyl with 3 to 12, particularly preferred with 3 to 6 carbon atoms.

$C_3$–$C_{12}$cycloalkyl is typically, cyclopropyl, cyclobutyl, cyclopentyl, methylcyclopentyl, dimethylcyclopentyl, cyclohexyl, methylcyclohexyl.

Cycloalkyl which is interrupted by at least one O or N atom is for example 2-tetrahydropyran-yl, tetrahydrofurane-yl, 1,4 dioxan-yl, pyrrolidin-yl, tetrahydrothiophen-yl, pyrazolidin-yl, imidazolidin-yl, butyrolactone-yl, caprolactame-yl.

$C_7$–$C_9$phenylalkyl is for example benzyl, phenylethyl or phenylpropyl.

$C_3$–$C_{18}$alkyl interrupted by at least one O atom is for example —CH$_2$—CH$_2$—O—CH$_2$—CH$_3$, —CH$_2$—CH$_2$—O—CH$_3$ or —CH$_2$—CH$_2$—O—CH$_2$—CH$_2$—CH$_2$—O—CH$_2$—CH$_3$. It is preferably derived from polyethlene glycol. A general description is —((CH$_2$)$_a$—O)$_b$—H/CH$_3$, wherein a is a number from 1 to 6 and b is a number from 2 to 10.

Y may be any substituent which facilitates Michael addition at the double bond. Preferably Y is CN, C(O)halogen, COOR$_4$, C(O)R$_4$, CONR$_5$R$_6$, phenyl or naphthyl which are unsubstituted or substituted by $C_1$–$C_4$alkyl, $C_1$–$C_4$alkoxy, $C_1$–$C_4$alkylthio, halogen, nitro, cyano, hydroxy, carboxy, $C_1$–$C_4$alkylamino or di($C_1$–$C_4$alkyl)amino; and R$_4$, R$_5$ and R$_6$ are hydrogen or $C_1$–$C_{18}$alkyl.

More preferably Y is CN, COOR$_4$ or phenyl which is unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; and R$_4$ is $C_1$–$C_4$alkyl.

Most preferably Y is CN, COOCH$_3$, COOC$_2$H$_5$ or phenyl.

X is halogen or the anion of a mono carboxylic acid from 1–12 carbon atoms, a monovalent oxo acid or complex acid. Examples of monocarboxylic acids with 1 to 12 carbon atoms are formic acid, acetic acid, propionic acid, phenyl acetic acid, cyclohexane carbonic acid, mono-, di- and trichlor-acetic acid or mono-, di- and trifluor-acetic acid. Other suitable acids are benzoic acid, chlorbenzoic acid, methanesulfonic acid, ethanesulfonic acid, benzenesulfonic acid, p-toluenesulfonic acid, chlorbenzenesulfonic acid, trifluormethanesulfonic acid, methylphosphonic acid or phenylphosphonic acid.

Preferably X is —Cl, —Br, —I, ClO$_4^-$, CF$_3$SO$_3^-$, CH$_3$SO$_3^-$, HSO$_4^-$, BF$_4^-$, B(Phenyl)$_4^-$, PF$_6^-$, SbCl$_6^-$, AsF$_6^-$ or SbF$_6^-$.

Further suitable anions are derived from alkyl-arylborates which are disclosed for example in U.S. Pat. No. 4,772,530, GB 2307474, GB 2307473, GB 2307472, EP 775706. Examples are triphenylbutylborate, triphenylhexylborate, triphenylmethylborate, dimesitylphenyl-methyl- or -butylborate, di(bromomesityl)-phenyl-methyl- or -butylborate, tris(3-fluorphenyl)-hexylborate, tris(3-fluorphenyl)-methyl- or -butylborate, dichloromesityl-phenyl-methyl- or -butylborate, tris(dichloromesityl)-methylborate, tris(3-chlorphenyl)-hexylborate, tris(3-chlorphenyl)-methyl- or -butylborate, tris(3-bromphenyl)-hexylborate, tris(3-bromphenyl)-methyl- or -butylborate, tris(3,5-difluorphenyl)-hexylborate, dimesityl-biphenyl-butylborate, dimesityl-naphthylmethyl- or -butylborate, di(o-tolyl)-9-anthracyl-methyl- or -butylborate, dimesityl-9-phenanthryl-phenyl- or -butylborate More preferably X is Cl$^-$, Br$^-$, ClO$_4^-$, CF$_3$SO$_3^-$, CH$_3$SO$_3^-$, CF$_3$COO$^-$, BF$_4^-$, or PF$_6^-$.

Most preferably X is Br$^-$.

Preferably n is 0.

In a preferred embodiment $R_1$, $R_2$, $R_3$ are independently of each other unsubstituted $C_1$–$C_{18}$alkyl, $C_3$–$C_{18}$alkyl interrupted by at least one nitrogen or oxygen atom, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_3$–$C_{18}$alkyl interrupted by at least one nitrogen or oxygen atom, $C_7$–$C_9$phenylalkyl, $C_3$–$C_{12}$cycloalkyl or $C_3$–$C_{12}$cycloalkyl containing at least one nitrogen or oxygen atom, which are substituted by NO$_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, which is unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or $R_1$ and $R_2$, together with the linking hetero atom, form a $C_4$–$C_7$heterocycloalkyl radical; or $R_1$ and $R_2$ form a group,

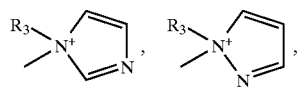

or $R_1$, $R_2$ and $R_3$ form a group

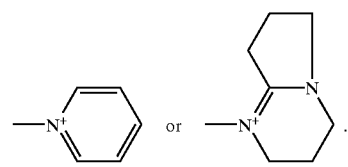

More preferably $R_1$, $R_2$ and $R_3$ independently of each other are unsubstituted $C_1$–$C_{12}$alkyl, $C_3$–$C_{12}$alkyl interrupted by at least one nitrogen or oxygen atom, benzyl or phenyl, which is unsubstituted or substituted by $C_1$–$C_4$alkyl, $C_1$–$C_4$alkoxy, $C_1$–$C_4$alkylthio, halogen, cyano, hydroxy, carboxy.

In a preferred subgroup of compounds of formula (Ia), (Ib) or (Ic) Y is CN, C(O)halogen, COOR$_4$, phenyl which is unsubstituted or substituted by $C_1$–$C_4$alkyl, $C_1$–$C_4$alkoxy, $C_1$–$C_4$alkylthio, halogen, cyano, hydroxy, carboxy, $R_4$, is $C_1$–$C_8$alkyl;

X is Br$^-$, ClO$_4^-$, CF$_3$SO$_3^-$, CH$_3$SO$_3^-$, CF$_3$COO$^-$, BF$_4^-$ or PF$_6^-$; and $R_1$, $R_2$ and $R_3$ independently of each other are unsubstituted $C_1$–$C_{12}$alkyl, $C_3$–$C_{12}$alkyl interrupted by at least one nitrogen or oxygen atom, benzyl or phenyl, which is unsubstituted or substituted by $C_1$–$C_4$alkyl, $C_1$–$C_4$alkoxy, $C_1$–$C_4$alkylthio, halogen, cyano, hydroxy, carboxy.

Preferred are compounds of formula (Ia).

Preferably the radical initiator b) is present in an amount of 0.01 to 5 weight % based on the monomer or monomer mixture.

Preferably the compound of formula (Ia), (Ib) or (Ic) is present in an amount of 0.01 to 10 weight % based on the monomer or monomer mixture.

The ratio of radical initiator to the compound of formula (Ia), (Ib) or (Ic) is preferably 0.1 to 10, more preferably 0.1 to 5 and most preferably 0.1 to 1.

The polymerization reaction may be carried out using photoinitiated radical polymerization. Photoinitiators useful in the present invention are of any known class. In certain cases it may be of advantage to use mixtures of two or more photoinitiators. Typical classes of photoinitators are for example camphor quinone, benzophenone, benzophenone derivatives, acetophenone, acetophenone derivatives, for example α-hydroxycycloalkyl phenyl ketones or 2-hydroxy-2-methyl-1-phenyl-propanone, dialkoxyacetophenones, α-hydroxy- or α-amino-acetophenones, e.g. (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, e.g. dimethyl benzil ketal, phenylglyoxalic esters and derivatives thereof, dimeric phenylglyoxalic esters, peresters, e,g. benzophenone tetracarboxylic peresters as described for example in EP 126541, monoacyl phosphine oxides, e.g. (2,4,6-trimethylbenzoyl)diphenylphosphine oxide, bisacylphosphine oxides, bis(2,6-dimethoxybenzoyl)-(2,4,4-trimethyl-pentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaarylbisimidazole/coinitiators systems, e.g. ortho-chlorohexaphenyl-bisimidazole combined with 2-mercaptobenzthiazole, ferrocenium compounds, or titanocenes, e.g. bis (cyclopentadienyl)-bis(2,6-difluoro-3-pyrryl-phenyl) titanium.

The photopolymerizable compositions generally comprise 0.05 to 15% by weight, preferably 0.1 to 5% by weight, of the photoinitiator, based on the composition. The amount refers to the sum of all photoinitiators added, if mixtures of initiators are employed.

Preferred compounds are of the α-hydroxyketone type, phosphorus containing photoinitators as well as the mixture of α-hydroxyketone compounds with phosphorous containing photoinitiators.

Preferred photoinitiators are of the formula PI

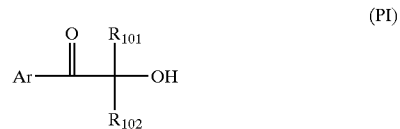

(PI)

wherein

Ar is unsubstituted phenyl or phenyl substituted by halogen, CN, OH, $C_1$–$C_{17}$alkoxy, phenoxy, $C_2$–$C_{12}$alkenyl, —S—$C_1$–$C_{12}$alkyl, —S-phenyl, —SO$_2$—$C_1$–$C_{12}$alkyl, —SO$_2$-phenyl, —SO$_2$NH$_2$, —SO$_2$NH—$C_1$–$C_{12}$alkyl, —SO$_2$—N($C_1$–$C_{12}$-alkyl)$_2$, —NH—$C_1$–$C_{12}$alkyl, —N($C_1$–$C_{12}$alkyl)$_2$ or —NH—CO-phenyl, isocyanate or masked isocyanate, or Ar is substituted with $C_1$–$C_{12}$alkyl, which $C_1$–$C_{12}$alkyl is unsubstituted or substituted by halogen, OH, CN, NH$_2$, COOH, isocyanate, masked isocyanate, alkenyl or masked alkenyl, or Ar is thienyl, pyridyl, furyl, indanyl or tetrahydronaphthyl;

$R_{101}$ is $C_1$–$C_8$alkyl, which is unsubstituted or substituted by OH, CN, NH$_2$, —NHC$_1$–C$_{12}$alkyl, N($C_1$–$C_{12}$alkyl)$_2$, NH—CO-phenyl, isocyanate or masked isocyanate, $C_2$–$C_{12}$alkenyl, halogen, $C_1$–$C_{12}$alkoxy, COOH, —(CO)O—$C_1$–$C_{12}$alkyl, —O—(CO)—$C_1$–$C_8$alkyl or NR$_{103}$R$_{104}$, or $R_{101}$ is $C_3$–$C_5$alkenyl, cyclopentyl, cyclohexyl or phenyl-$C_1$–$C_3$alkyl;

$R_{102}$ has one of the meanings given for $R_{101}$, or is a group —CH$_2$CH$_2$R$_5$, or $R_{102}$ together with $R_{101}$ is $C_2$–$C_8$alkylene, $C_3$–$C_9$oxaalkylene, $C_3$–$C_9$azaalkylene, or an exomethylene cyclohexane ring, wherein the $C_2$–$C_8$alkylene, $C_3$–$C_9$oxaalkylene, $C_3$–$C_9$azaalkylene, or exomethylene cyclohexane ring is unsubstituted or substituted by OH, CN, halogen, $C_1$–$C_{12}$alkoxy, —(CO)O—$C_1$–$C_{12}$alkyl, —O—(CO)—$C_1$–$C_8$alkyl or NR$_{103}$R$_{104}$;

$R_{103}$ is $C_1$–$C_{12}$alkyl, $C_2$–$C_4$alkyl which is substituted by OH, $C_1$–$C_8$alkoxy or CN, or $R_{103}$ is $C_3$–$C_5$alkenyl, cyclohexyl, phenyl-$C_1$–$C_3$alkyl, unsubstituted phenyl or phenyl, which is substituted by Cl, $C_1$–$C_4$alkyl, OH, $C_1$–$C_4$alkoxy or —(CO)O—$C_1$–$C_8$alkyl;

$R_{104}$ is $C_1$–$C_{12}$alkyl, $C_2$–$C_4$alkyl which is substituted by OH, $C_1$–$C_8$alkoxy or CN, or $R_{104}$ is $C_3$–$C_5$alkenyl, cyclohexyl or phenyl-$C_1$–$C_3$alkyl, or $R_{104}$ together with $R_{103}$ is $C_4$–$C_5$alkylene, which may be interrupted by —O— or —NR$_{106}$—, or $R_{104}$ together with $R_{102}$ is $C_1$–$C_9$alkylene, $C_2$–$C_{30}$oxaalkylene or $C_2$–$C_3$azaalkylene;

$R_{105}$ is —CO—NH$_2$, —CO—NH—$C_1$–$C_8$alkyl, —CO—N($C_1$–$C_8$alkyl)$_2$, —P(O)(O—$C_1$–$C_8$alkyl)$_2$ 2-pyrridyl or 2-oxo-1-pyrroldinyl; and $R_{106}$ is $C_1$–$C_4$alkyl, —CH$_2$CH$_2$CN or —CH$_2$CH$_2$(CO)O—$C_1$–$C_8$alkyl.

$C_1$–$C_{17}$alkoxy is linear or branched and is for example $C_1$–$C_{12}$alkoxy, $C_1$–$C_8$- or $C_1$–$C_6$alkoxy, especially $C_1$–$C_4$alkoxy. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy, dodecyloxy, tetradecyloxy, pentadecyloxy, hexadecyloxy or heptadecyloxy especially methoxy, ethoxy, propoxy, isopropoxy, n-butyloxy, sec-butyloxy, iso-butyloxy, tert-butyloxy, preferably methoxy. $C_1$–$C_{12}$alkoxy, $C_1$–$C_8$alkoxy and $C_1$–$C_4$alkoxy have the same meanings as given above up to the appropriate number of C-atoms.

$C_2$–$C_{12}$alkenyl is one or more times unsaturated and is for example $C_2$–$C_8$-alkenyl, $C_2$–$C_6$- or $C_3$–$C_5$-alkenyl, especially $C_2$–$C_4$-alkenyl. Examples are allyl, methallyl, 1,1-dimethylallyl, 1-butenyl, 3-butenyl, 2-butenyl, 1,3-pentadienyl, 5-hexenyl, 7-octenyl, nonenyl, dodecenyl, especially allyl. $C_3$–$C_5$alkenyl has the same meanings as given above up to the appropriate number of C-atoms.

$C_1$–$C_{12}$alkyl is linear or branched and is for example $C_1$–$C_{10}$-, $C_1$–$C_8$- or $C_1$–$C_6$alkyl, especially $C_1$–$C_4$alkyl. Examples are methyl, ethyl, propyl, isopropyl, n-butyl, sec-butyl, iso-butyl, tert-butyl, pentyl, hexyl, heptyl, 2,4,4-trimethyl-pentyl, 2-ethylhexyl, octyl, nonyl, decyl, undecyl or dodecyl, preferably methyl or butyl. $C_1$–$C_8$alkyl and $C_2$–$C_4$alkyl have the same meanings as given above up to the appropriate number of C-atoms. In the terms —S—$C_1$–$C_{12}$alkyl, —$SO_2$—$C_1$–$C_{12}$alkyl, —COO—$C_1$–$C_{12}$alkyl, —$SO_2$NH—$C_1$–$C_{12}$alkyl, —$SO_2$—N($C_1$–$C_{12}$-alkyl)$_2$, —NH—$C_1$–$C_{12}$alkyl and —N($C_1$–$C_{12}$alkyl)$_2$, $C_1$–$C_{12}$alkyl has the meanings given above. In the groups —O—(CO)—$C_1$–$C_8$alkyl, —CO—NH—$C_1$–$C_8$alkyl, —CO—N($C_1$–$C_8$alkyl)$_2$, —$CH_2CH_2$(CO)O—$C_1$–$C_8$alkyl and —P(O)(O—$C_1$–$C_8$alkyl)$_2$ $C_1$–$C_8$alkyl has the same meanings as given above. If $C_1$–$C_{12}$alkyl is substituted with halogen, there are, for example 1 to 3 or 1 or 2 halogen substituents located at the alkyl.

The term "masked isocyanate" means a protected isocyanate group, namely an isocyanate group, which is blocked by chemical groups, which under specific reaction conditions can be removed. So, the formation of an oxime results in a masked isocyanate group. Examples are given, for example in J. Coatings Technology, Vol. 61, No. 775 (August 1989). The blocking/deblocking mechanism is, for example, demonstrated by the following equation: R—N—(CO)—X (blocked isocyanate)⇌R—N=C=O+HX On the left side the blocked isocyanate is not susceptible to reactions in the formulation, while on the right side the influence of temperature (>120° C.) deblocks HX and liberates the isocyanate group, which is now able to take part in further reactions, for example with crosslinkers. Suitable blocking agents HX are, for example, phenol, caprolactam, methyl ethyl ketoxime and diethyl malonate.

Phenyl-$C_1$–$C_3$alkyl is, for example, benzyl, phenylethyl, α-methylbenzyl, Phenylpropyl, or α,α-dimethylbenzyl, especially benzyl.

$C_2$–$C_8$alkylene is linear or branched alkylene as, for example, methylene, ethylene, propylene, 1-methylethylene, 1,1-dimethylethylene, butylene, 1-methylpropylene, 2-methylpropylene, pentylene, hexylene, heptylene or octylene, especially hexylene. $C_4$–$C_5$alkylene is linear or branched, for example, 1,1-dimethylethylene, butylene, 1-methylpropylene, 2-methylpropylene or pentylene. $C_4$–$C_5$alkylene, which may be interrupted by —O— or —$NR_{106}$—, is, for example, —$CH_2CH_2$—O—$CH_2CH_2$—, —$CH_2CH_2$—(NR$_{106}$)—$CH_2CH_2$—, —$CH_2$—O—$CH_2CH_2CH_2$—, —$CH_2$—(NR$_{106}$)—$CH_2CH_2CH_2$— or —$CH_2CH_2$—O—$CH_2CH_2CH_2$—. $C_3$–$C_9$oxaalkylene can contain, for example, 1–3 or 1 or 2 O-atoms, especially 1 O-atom and means for example, —$CH_2$—O—$CH_2$—, —$CH_2CH_2O$—$CH_2CH_2$—, —$CH_2$—CH(CH$_3$)—O—$CH_2CH_2CH_2$— or —[$CH_2CH_2O$]$_y$—, wherein y=1–4. $C_3$–$C_9$azaalkylene can contain, for example, 1–3 or 1 or 2 (NR$_{106}$)-groups, especially 1 such group and means, for example, —$CH_2$—(NR$_{106}$)—$CH_2$—, —$CH_2CH_2$—(NR$_{106}$)—$CH_2CH_2$—, —$CH_2$—CH(CH$_3$)—(NR$_{106}$)—$CH_2CH_2CH_2$— or —[$CH_2CH_2(NR_{106})$]$_y$— wherein y=1–4 and wherein $R_{106}$ has the meanings given above.

The exomethylen cyclohexane ring has the following structure

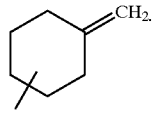

Halogen is fluorine, chlorine, bromine and iodine, especially chlorine and bromine, preferably chlorine.

Preferably Ar in the formula I is unsubstituted phenyl or phenyl substituted by $C_1$–$C_{12}$alkyl or phenyl substituted by $C_1$–$C_4$alkyl, which is substituted with OH, $R_{101}$ and $R_{102}$ are $C_1$–$C_4$alkyl, or $R_{102}$ together with $R_{101}$ and the C-atom to which they are bonded, are $C_2$–$C_8$alkylene.

Suitable compounds of the formula I are phenyl-1-hydroxycyclohexylketone (®Irgacure 184; Ciba-Geigy AG);

4-dodecylphenyl-2-hydroxy-prop-2-yl ketone;

4-isopropylphenyl-2-hydroxy-prop-2-yl ketone;

2-hydroxy-2-methyl-1-phenyl-propanone;

[4-(2-hydroxyethyl)-phenyl]-2-hydroxy-prop-2-yl ketone;

4-methylphenyl-2-hydroxy-prop-2-yl ketone

[4-(2-carboxyethyl)-phenyl]-2-hydroxy-prop-2-yl ketone. Especially preferred are phenyl-1-hydroxycyclohexylketone, 2-hydroxy-2-methyl-1-phenyl-propanone, [4-(2-hydroxyethyl)-phenyl]-2-hydroxy-prop-2-yl ketone and [4-(2-carboxyethyl)-phenyl]-2-hydroxy-prop-2-yl ketone. The photoinitators according to the formula I are known, some of the compounds are commercially available and the art-skilled is familiar with their preparation. The compounds and their preparation are, for example, disclosed in U.S. Pat. Nos. 4,308,400; 4,315,807; 4,318,791; 4,721,734; 4,347,111; 4,477,681; 4,861,916; 5,045,573.

Preferred is also a mixture of photoinitiators of at least one compound of the formula I and at least one phosphorus containing photoinitator of the formula IIa or IIb

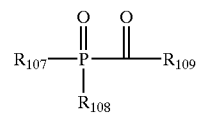

(IIa)

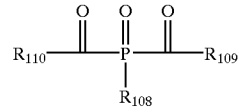

(IIb)

wherein $R_{107}$ and $R_{108}$ independently of one another are $C_1$–$C_{18}$alkyl, cyclohexyl, cyclopentyl, phenyl, naphthyl or biphenyl, wherein the cyclohexyl, cyclopentyl, phenyl, naphthyl or biphenyl are unsubstituted or substituted by halogen, $C_1$–$C_{12}$alkyl and/or $C_1$–$C_{12}$alkoxy, or $R_7$ and $R_8$ are a 5- or 6-membered S- or N-containing heterocyclic ring;

$R_{109}$ and $R_{110}$ independently of one another are cyclohexyl, cyclopentyl, phenyl, naphthyl or biphenyl, which residues are unsubstituted or substituted by halogen, $C_1$–$C_4$alkyl and/or $C_1$–$C_4$alkoxy, or $R_{109}$ and $R_{110}$ are a 5- or 6-membered S- or N-containing heterocyclic ring, or $R_{109}$ and $R_{110}$ together with the P-atom to which they are bonded from a ring, which contains from 4 to 10 carbon atoms and which ring may be substituted by 1 to 6 $C_1$–$C_4$alkyl radicals.

$C_1$–$C_{18}$Alkyl is branched or unbranched alkyl and is, for example, $C_1$–$C_{12}$-, $C_1$–$C_{10}$-, $C_1$–$C_8$- or $C_1$–$C_6$-alkyl, especially $C_1$–$C_4$alkyl. Examples are methyl, ethyl, propyl, isopropyl, n-butyl, sec-butyl, tert-butyl, pentyl, hexyl, heptyl, octyl, 2-ethylhexyl, 2,4,4-trimethyl-pentyl, decyl, dodecyl, tetradecyl, heptadecyl or octadecyl. $C_1$–$C_{12}$alkyl has the same meanings as given above up to the appropriate number of C-atoms Preferably $R_{108}$ as alkyl is $C_4$–$C_8$alkyl, for example n-butyl, tert-butyl, isobutyl, sec-butyl, n-octyl, 2,4,4-trimethylpentyl.

$C_1$–$C_{12}$alkoxy is linear or branched and is for example $C_1$–$C_8$- or $C_1$–$C_6$alkoxy, especially $C_1$–$C_4$alkoxy. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy, tert-butyloxy, preferably methoxy.

Halogen is fluorine, chlorine, bromine and iodine, especially chlorine and bromine, preferably chlorine.

Naphthyl means α-naphthyl and β-naphthyl.

Substituted cyclopentyl, cyclohexyl, phenyl, naphthyl or biphenyl have, for example 1-5, 1-4, three, two or one substituents. For substituted phenyl the substitution in 4-, 2,5-, 2-, 2,6- or 2,4,6-position is preferred. Examples for such groups are 4-chlorophenyl, 2,6-dichlorophenyl, 2,4,6-trichlorophenyl, difluorophenyl, 2-tolyl, 4-tolyl, ethylphenyl, tert-butylphenyl, dodecylphenyl, 4-methoxyphenyl, 2-methoxyphenyl, 2,6-dimethoxyphenyl, ethoxyphenyl, hexyloxyphenyl, 2,4-dimethylphenyl, 2,4,6-trimethylphenyl, methylnaphthyl, isopropylnaphthyl, chloronaphthyl or ethoxynaphthyl. Furthermore, such groups are, for example, methoxyethylphenyl, ethoxymethylphenyl.

$R_{109}$ and $R_{110}$ preferably are substituted phenyl, for example 2,6-dimethoxyphenyl, 2,6-dichlorphenyl, 2,4,6-trimethylphenyl, especially 2,4,6-trimethylphenyl. A 5- or 6-membered S- or N-containing heterocyclic ring is, for example, thienyl, pyrryl, pyrazolyl, thiazolyl, pyridyl or 1,3-, 1,2- or 1,4-diazyl, preferably thienyl or pyrryl.

If $R_{109}$ and $R_{110}$ together with the P-atom to which they are bonded form a ring containing 4 to 10 C-atoms this ring is monocyclic, bicyclic or tricyclic. A monocyclic ring formed by $R_{109}$ and $R_{110}$ together with the P-atom is preferably a phosphacyclopentane ring. A bicyclic ring formed by $R_{109}$ and $R_{110}$ together with the P-atom is preferably a phosphabicyclohexane or phosphabicyclononane ring. A tricyclic ring formed by $R_{109}$ and $R_{110}$ together with the P atom is preferably a (6H)-dibenzo[c,e][1,2]oxaphosphorine ring.

$R_{109}$ and $R_{110}$ are preferably 2,6-dimethoxyphenyl, 2,6-dimethylphenyl, 2,6-dichlorophenyl or especially 2,4,6-trimethylphenyl.

$R_{107}$ and $R_{108}$ preferably are $C_1$–$C_{18}$alkyl, cyclohexyl, cyclopentyl, phenyl or phenyl substituted with $C_1$–$C_4$alkyl. Specifically preferred $R_{107}$ and $R_{108}$ are n-butyl, tert-butyl, isobutyl, sec-butyl, n-octyl, 2,4,4-trimethylpentyl, phenyl or 2,5-dimethylphenyl.

The photoinitators according to the formulae IIa and IIb are known, some are commercially available compounds and the art-skilled is familiar with their preparation. The compounds and their preparation are, for example, disclosed in U.S. Pat. Nos. 4,792,632; 4,737,593; 4,298,738; 5,218,009; 5,399,770; 5,472,992.

Suitable compounds of the formula IIa and IIb are
2,4,6-trimethylbenzoyl-diphenyl-phosphine oxide;
bis(2,4,6-trimethylbenzoyl)-2,4-di(3-methyl-but-1-oxy) phenyl-hosphine oxide;
bis(2,4,6-trimethylbenzoyl)-2,4-dipentoxyphenyl-phosphine oxide;
bis(2,4,6-trimethylbenzoyl)-2-methyl-prop-1-yl-phosphine oxide;
bis(2,6-dimethoxybenzoyl)-2,4,4-trimethylpent-1-yl-phosphine oxide;
bis(2,4,6-trimethylbenzoyl)-phenyl phosphine oxide;

Examples for photoinitiator mixtures suitable for the instant processes are
a mixture of bis(2,6-dimethoxybenzoyl)-2,4,4-trimethylpent-1-yl-phosphine oxide with 2-hydroxy-2-methyl-1-phenyl-propanone;
a mixture of 2-hydroxy-2-methyl-1-phenyl-propanone with (2,4,6-trimethylbenzoyl)-diphenyl phosphine oxide;
a mixture of phenyl-1-hydroxycyclohexylketone with bis(2,6-dimethoxybenzoyl)-2,4,4-trimethylpent-1-yl-phosphine oxide;
a mixture of phenyl-1-hydroxycyclohexylketone with bis(2,4,6-trimethylbenzoyl)-2-methyl-prop-1-yl-phosphine oxide;
a mixture of phenyl-1-hydroxycyclohexylketone with bis(2,4,6-trimethylbenzoyl)-phenyl phosphine oxide;
a mixture of phenyl-1-hydroxycyclohexylketone with bis(2,4,6-trimethylbenzoyl)-2,4-dipentoxyphenyl-phosphine oxide;
a mixture of 2-hydroxy-2-methyl-1-phenyl-propanone with bis(2,4,6-trimethylbenzoyl)-2-methyl-prop-1-yl-phosphine oxide;
a mixture of 2-hydroxy-2-methyl-1-phenyl-propanone with bis(2,4,6-trimethylbenzoyl)-phenyl phosphine oxide;
a mixture of 2-hydroxy-2-methyl-1-phenyl-propanone with bis(2,4,6-trimethylbenzoyl)-2,4-dipentoxyphenyl-phosphine oxide.

The range of the α-hydroxyketone photoinitiator, compounds of the formula PI respectively, in the mixtures of these compounds with phosphorus containing photoinitiators, compounds of the formula IIa or IIb respectively, is, for example 50–95% by weight. Preferably the amount of the compounds of the formula I in the mixture is 50–75%, especially 75% (based on 100% by weight of the total mixture).

Of interest is a process, wherein the formula PI Ar is unsubstituted phenyl or phenyl substituted by $C_1$–$C_{12}$alkyl, which $C_1$–$C_{12}$alkyl is unsubstituted or substituted by OH or COOH, $R_{101}$ and $R_{102}$ are $C_1$–$C_{18}$alkyl or $R_{101}$ together with $R_{102}$ is $C_2$–$C_8$alkylene, and wherein the formula IIa or the formula IIb $R_{107}$ and $R_{108}$ independently of one another are $C_1$–$C_{12}$alkyl or phenyl, wherein the phenyl is unsubstituted or substituted by $C_1$–$C_8$alkyl and/or $C_1$–$C_8$alkoxy and $R_{109}$ and $R_{110}$ independently of one another are phenyl, which is substituted by halogen, $C_1$–$C_4$alkyl and/or $C_1$–$C_4$alkoxy.

Preferred is, for example, a mixture of 2-hydroxy-2methyl-1-phenyl-propanone with bis(2,6-dimethoxybenzoyl)-2,4,4-trimethylpent-1-yl-phosphine oxide. Especially preferred is the above mixture with an amount of 2-hydroxy-2methyl-1-phenyl-propanone of 75% by weight.

Also preferred, for example, is a mixture of 2-hydroxy-2methyl-1-phenyl-propanone with 2,4,6-trimethylbenzoyl-phenyl-phosphine oxide. Especially preferred is the above mixture with an amount of 2-hydroxy-2methyl-1-phenyl-propanone of 50% by weight.

The composition to be (co)polymerized in the instant process expediently contains the photoinitiator of the formula PI, IIa or IIb, or the photoinitiator mixture of the compounds of the formulae I and IIa or IIb in an amount of from 0.1 to 15% by weight, preferably from 0.2 to 5% by weight, based on the total solids content.

Additional coinitiators or sensitizers may be used. These are typically dyes which react by energy transfer or electron transfer and such enhance the overall quantum yield. Typical dyes are for example triarylmethane, such as malachit green, indoline, thiazine, such as methylen blue, xanthone, thioxanthone, oxazine, acridine or phenazine, such as safranine, or rhodamine of formula

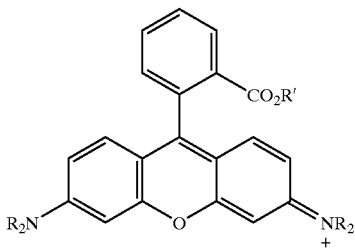

wherein R is alkyl or aryl and R' is hydrogen, alkyl or aryl. Examples are Rhodamin B, Rhodamin 6G oder Violamin R, Sulforhodamin B or Sulforhodamin G.

Preferred are thioxanthone, oxazine, acridine, phenazine or rhodamine. The polymerization reaction may also be carried out using thermally initiated radical polymerization. The source of radicals may be a bis-azo compound, a peroxide or a hydroperoxide.

Most preferably, the source of radicals is 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1'-azobis(-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1-bis(hydroxymethyl)ethyl]propionamide} or 2,2'-azobis{2-methyl-N-[1,1-bis(hydroxymethyl)-2-hydroxyethyl]propionamide. Preferred peroxides and hydroperoxides are acetyl cyclohexane sulphonyl peroxide, diisopropyl peroxy dicarbonate, t-amyl perneodecanoate, t-butyl perneodecanoate, t-butyl perpivalate, t-amylperpivalate, bis (2,4-dichlorobenzoyl)peroxide, diisononanoyl peroxide, didecanoyl peroxide, dioctanoyl peroxide, dilauroyl peroxide, bis (2-methylbenzoyl)peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy) 3,5,5-trimethylcyclohexane, 1,1-bis(t-butylperoxy) cyclohexane, t-butyl peroxy isopropyl carbonate, t-butyl perisononaoate, 2,5-dimethylhexane 2,5-dibenzoate, t-butyl peracetate, t-amyl perbenzoate, t-butyl perbenzoate, 2,2-bis (t-butylperoxy)butane, 2,2bis (t-butylperoxy)propane, dicumyl peroxide, 2,5-dimethylhexane-2,5-di-t-butylperocide, 3-t-butylperoxy 3-phenylphthalide, di-t-amyl peroxide, α,α'-bis(t-butylperoxy isopropyl)benzene, 3,5-bis (t-butylperoxy)3,5-dimethyl 1,2-dioxolane, di-t-butyl peroxide, 2,5-dimethylhexyne-2,5-di-t-butylperoxide, 3,3,6, 6,9,9-hexamethyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

These compounds are commercially available.

Typically the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl) acrylic acidanhydrides, (alkyl)acrylic acid salts, (alkyl) acrylic esters, (meth)acrylonitriles, (alkyl)acrylamides, vinyl halides or vinylidene halides. Preferred ethylenically unsaturated monomers are ethylene, propylene, n-butylene, i-butylene, isoprene, 1,3-butadiene, $\alpha$-$C_5$–$C_{18}$alkene, styrene, $\alpha$-methyl styrene, p-methyl styrene or a compound of formula $CH_2=C(R_a)-(C=Z)-R_b$, where in $R_a$ is hydrogen or $C_1$–$C_4$alkyl, $R_b$ is $NH_2$, $O^-(Me^+)$, glycidyl, unsubstituted $C_1$–$C_{18}$alkoxy, $C_2$–$C_{100}$alkoxy interrupted by at least one N and/or O atom, or hydroxy-substituted $C_1$–$C_{18}$alkoxy, unsubstituted $C_1$–$C_{18}$alkylamino, di($C_1$–$C_{18}$alkyl)amino, hydroxy-substituted $C_1$–$C_{18}$alkylamino or hydroxy-substituted di($C_1$–$C_{18}$alkyl) amino, $-O-CH_2-CH_2-N(CH_3)_2$ or $-O-CH_2-CH_2-N^+H(CH_3)_2An^-$; $An^-$ is a anion of a monovalent organic or inorganic acid; Me is a monovalent metal atom or the ammonium ion. Z is oxygen or sulfur.

Examples for $R_a$ as $C_2$–$C_{100}$alkoxy interrupted by at least one O atom are of formula

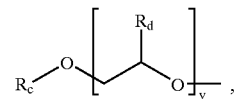

wherein $R_c$ is $C_1$–$C_{25}$alkyl, phenyl or phenyl substituted by $C_1$–$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

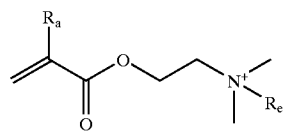

An- or

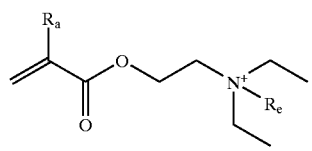

$An^-$, wherein $An^-$ and $R_a$ have the meaning as defined above and $R_e$ is methyl or benzyl. $An^-$ is preferably $Cl^-$, $Br^-$ or $^-O_3S-CH_3$.

Further acrylate monomers are

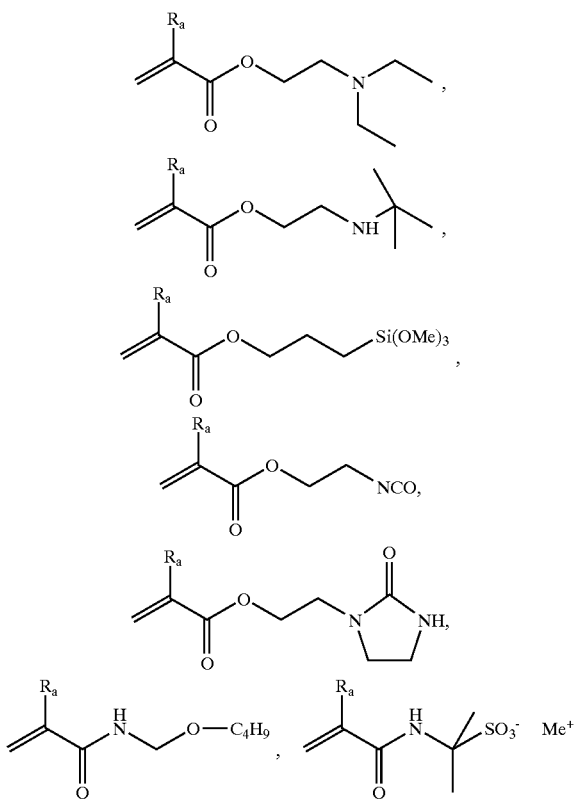

Examples for suitable monomers other than acrylates are

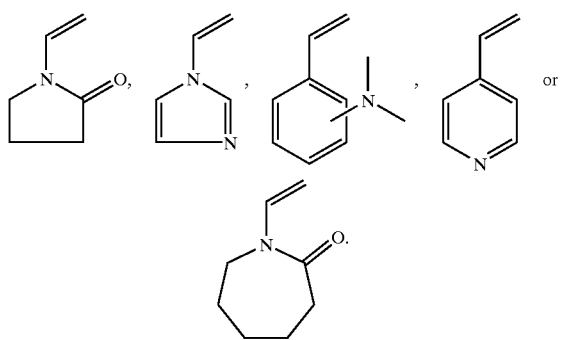

Preferably $R_a$ is hydrogen or methyl, $R_b$ is $NH_2$, gycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino; and Z is oxygen.

Particularly preferred ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl (meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth) acrylates, acrylonitrile, acrylamide, methacrylamide or dimethylaminopropyl-methacrylamide.

Another subject of the present invention is a process for preparing an oligomer, a cooligomer, a polymer or a copolymer (block or random) by free radical polymerization of a) at least one ethylenically unsaturated monomer or oligomer, which comprises (co)polymerizing the monomer or monomers/oligomers in the presence of b) a radical initiator which forms a radical upon heating or upon irradiation with (UV) light from 305 nm to 450 nm and c) a compound of formula (Ia), (Ib) or (Ic) according to claim 1 by subjecting the mixture to heat or electromagnetic radiation in the wavelength range from 305 nm to 450 nm.

Definitions and preferences for the different substituents have already been given and apply also for the polymerization process.

Preferably the radical initiator b) is present in an amount of 0.01 to 5 weight % based on the monomer or monomer mixture.

Preferably the compound of formula (Ia), (Ib) or (Ic) is present in an amount of 0.01 to 10 weight % based on the monomer or monomer mixture.

The ratio of radical initiator to the compound of formula (Ia), (Ib) or (Ic) is preferably 0.1 to 10, more preferably 0.1 to 5 and most preferably 0.1 to 1.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%. In many cases it is possible to polymerize without any solvent, particularly if the process is carried out by photo initiated radical polymerization.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

Aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The oligomers/polymers prepared with the instant process can be used for various purposes, for example for the production of printing inks, varnishes, white paints, coating compositions, inter alia for paper, wood, metal or plastic, for the production of coloured pigmented paints, daylight-curable coatings for buildings and road markings, for the preparation of clear or pigmented aqueous dispersions, for the production of printing plates, for the production of masks for screen printing, as dental filling materials, for the production of adhesives, of etch or permanent resists and of solder stop masks for printed electronic circuits, for the production of three-dimensional articles by bulk curing (UV curing in transparent moulds) or for the production of formulations used in the stereolithography process, as described, for example, in U.S. Pat. No. 4,575,330, for the preparation of composite materials (for example styrenic polyesters, which may contain glass fibres and other assistants) and other thick-layer compositions, for the production of coatings for encapsulation of electronic parts or for the production of coatings for optical fibres.

A further subject of the present invention is a polymer or copolymer prepared by the above process containing a vinyl- or 1,3 dienyl group at one end of the molecule. Preferably the polymers have an average number molecular weight (Mn) of 1000–500 000 more preferably 5000–300 000, and most preferably 5000–100 000.

The polydispersity (PD) as defined by Mn/Mw is preferably below 3, more preferably from 1.1 to 2.5 and most preferably from 1.1 to 2.

The chain transfer coefficient $c_x$ is preferably from 0.4 to 1, more preferably from 0.6 to 1 and most preferably from 0.7 to 1.

The thermally initiated reaction may be carried out in any vessel suitable for radical polymerization reactions. Examples are known in the art.

Preferably the reaction temperature is kept between 60° C. and 120° C. Reaction time may vary, depending on the molecular weight desired. Typical reaction times are from 1 hour to 24 hours.

Photochemically initiated radical polymerization may be carried out for example in an apparatus as described in WO 98/37105.

The photoreactor used to prepare the examples is fabricated in Rodoxal, an aluminum alloy, but suitable reactors can also be constructed, for example in stainless steel or in any material compatible with the monomers employed, as for example teflon, brown glass etc. The reactor possesses a glass window allowing transmission of the UV-light. The overall irradiation surface of the reactor is 26 cm$^2$ and the cell thickness is 1 cm. In this connection the "overall irradiation surface" of the reactor means the surface of the irradiated part of the reactor, namely the window and the "cell thickness" is the thickness of the internal path (diameter) of the reactor at the irradiated part. The process can also be carried out using an optical bench and a UV-cell for absorption spectra fitted with a septum to allow reactions under argon and a magnetic stirrer. This UV-cell, similar to those used to measure UV-spectra, may be irradiated through a 2 cm$^2$ window with homogeneous light from a Philips 100 W medium pressure mercury lamp and the cooling may be effected through the side walls of the cell. Bigger reactor dimensions, as for example an overall irradiation surface (window size) of 26 cm$^2$ with a cell thickness (diameter) of 1 cm need lamps of higher output and bigger. irradiation surfaces such as, for example, Fusion Curing lamps F200 to F600. As those commercially available lamps have a bulb length of 6 inches (about 15.5 cm; F200 lamp) or 10 inches (about 25 cm; F600 lamp), the reactor should not exceed this height. The irradiation surface can thus be adapted to the necessary reaction conditions. Naturally, for the instant process it is also possible to employ reactors with other dimensions. The crucial point is to guarantee a controlable and homogenic generation of radicals of the photoinitiator throughout the reactor, which is achieved, by controling the flow of the mixture and the distribution of radicals in the mixture by stirring and appropriate irradiation. This is not dependent on the size of the reactor or the irradiation surface.

The reaction time depends on the intensity of the UV-lamp, the area of irradiation, monomer and initiator concentration and may thus vary in a very wide range, depending on the conditions actually used.

The reaction temperature of the photochemically induced polymerization is preferably kept between 20° and 70° C. The reaction time is preferably from 5 minutes to 5 hours, more preferably from 10 minutes to 2 hours.

A further subject of the present invention is the use of a compound of formulae (Ia), (Ib) or (Ic) according to claim 1 in a radical initiated polymerization process.

Yet another subject of the invention are new compounds according to formula (Xa), (Xb) or (Xc)

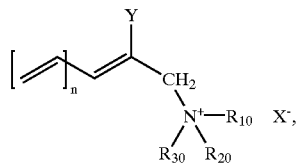

(Xa)

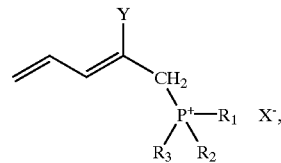

(Xb)

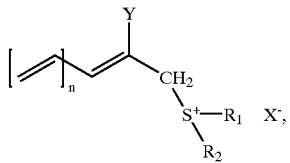

(Xc)

wherein
Y is CN, C(O)halogen, COOR$_4$, C(O)R$_4$, CONR$_5$R$_6$, phenyl or naphthyl which are unsubstituted or substituted by C$_1$–C$_4$alkyl, C$_1$–C$_4$alkoxy, C$_1$–C$_4$alkylthio, halogen, nitro, cyano, hydroxy, carboxy, C$_1$–C$_4$alkylamino or di(C$_1$–C$_4$alkyl)amino; and
R$_4$, R$_5$ and R$_6$ are hydrogen or C$_1$–C$_{18}$alkyl;
X is Cl$^-$, Br$^-$, —I$^-$, ClO$_4^-$, CF$_3$SO$_3^-$, CH$_3$SO$_3^-$, CF$_3$COO$^-$, p-toluene sulfonate, HSO$_4^-$, BF$_4^-$, PF$_6^-$, SbCl$_6^-$, AsF$_6^-$, SbF$_6^-$ or a mono carboxylic acid from 1–12 carbon atoms;
n is 0 or 1;
R$_1$, R$_2$ R$_3$ are independently of each other hydrogen, unsubstituted C$_1$–C$_{18}$alkyl, C$_3$–C$_{18}$alkyl, interrupted by at least one nitrogen or oxygen atom, C$_3$–C$_{18}$alkenyl, C$_3$–C$_{18}$alkynyl, C$_7$–C$_9$phenylalkyl, C$_3$–C$_{12}$cycloalkyl or C$_3$–C$_{12}$cycloalkyl containing at least one nitrogen or oxygen atom; or C$_3$–C$_{18}$alkyl, C$_3$–C$_{18}$alkyl, interrupted by at least one nitrogen or oxygen atom, C$_3$–C$_{18}$alkenyl, C$_3$–C$_{18}$alkynyl, C$_7$–C$_9$phenylalkyl, C$_3$–C$_{12}$cycloalkyl or C$_3$–C$_{12}$cycloalkyl containing at least one nitrogen or oxygen atom, which are substituted by NO$_2$, halogen, amino, hydroxy, cyano, carboxy, C$_1$–C$_4$alkoxy, C$_1$–C$_4$alkylthio, C$_1$–C$_4$alkylamino, di(C$_1$–C$_4$alkyl)amino or by a group —O—C(O)—C$_1$–C$_{18}$alkyl; or phenyl, naphthyl, which are unsubstituted or substituted by C$_1$–C$_4$alkyl, C$_1$–C$_4$alkoxy, C$_1$–C$_4$alkylthio, halogen, cyano, hydroxy, carboxy, C$_1$–C$_4$alkylamino or di(C$_1$–C$_4$alkyl)amino; or R$_1$ and R$_2$, together with the linking hetero atom, form a C$_3$–C$_{12}$ heterocycloalkyl radical; or R$_1$ and R$_2$ form a group,

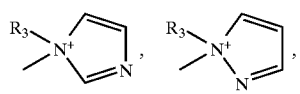

or

R$_1$, R$_2$ and R$_3$ form a group

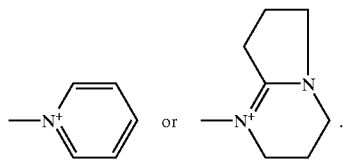

R$_{10}$ and R$_{20}$ are independently of each other C$_3$–C$_{18}$alkyl which is unsubstituted or substituted by NO$_2$, halogen, amino, hydroxy, cyano, carboxy, C$_1$–C$_4$alkoxy, C$_1$–C$_4$alkylthio, C$_1$–C$_4$alkylamino or di(C$_1$–C$_4$alkyl)amino; and R$_{30}$ is hydrogen or methyl.

Preferred are compounds of formula (Xa), wherein Y is phenyl, CN or COOR$_4$ and R$_4$ is C$_1$–C$_4$alkyl.

Preferably in the compounds of formula (Xa) X is Cl or Br.

Preferably in the compounds of formula (Xa) R$_2$ and R$_3$ are C$_6$–C$_{12}$alkyl.

The compounds of formula (Ia), (Ib), (Ic), X(a), X(b) and X(c) can be prepared according to known methods.

An analogous synthesis is for example described in U.S. Pat. No. 4,247,700 as well as in CA: 96 163229c. The synthesis of the acrylic and acrylonitrile derivatives is effected by Mannich reaction of the aliphatic amine with cyanacetic acid or monoesters of malonic acid in the presence of formaldehyde solutions in water, followed by reaction with an alkylating agent. The styrene equivalent is best synthesized in analogy to WO88/04304 starting from α-brommethyl styrene and the corresponding amine. Another possibility is described by in Melikyan et al. in Chemistry Papers 46 (4), 269–271 (1992) starting from the corresponding cinnamates.

The following examples illustrate the invention.

A) PREPARATION OF COMPOUNDS

Ammonium Salts with Y=CN

EXAMPLE A1

Preparation of 2-N,N-Dioctyl-aminomethyl 2-Acrylonitrile, Compound 101

The title compound is prepared according to EP-A-31584. 8.5 g (0.1 mol) cyano acetic acid and 24.15 g (0.1 mol) dioctylamine are dissolved in 150 ml dioxane and the mixture is cooled to 10° C. 50 ml of a 36% formaldehyde solution in water are added within 15 min under stirring and stirring is continued for another 15 min. Subsequently 150 ml of a 36% formaldehyde solution is added within 30 min at a temperature of 12–15° C. The solution is heated to room temperature and stirred for 3 h, followed by 2 h at 60° C. After cooling to room temperature the solvent is removed and the title compound is obtained in 100% yield. Elemental analysis % calculated C, H, N: 78.4, 12.5, 9.1; % found: 78.0, 12.2, 9.1.

EXAMPLE A2

2-N,N,N-Dioctylmethyl-ammoniummethyl-2-acrylonitrile, Compound 102

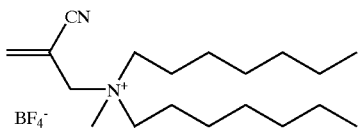

17.1 g of the compound of example A1 (55 mmol) are dissolved in 600 ml dry CH$_2$Cl$_2$ under argon atmosphere. 7.5 g (50.7 mmol) trimethyloxonium tetrafluoroborate are added in portions within 20 min under argon atmosphere. The mixture is stirred over night at room temperature and the solvent is evaporated. The raw product is dissolved in 200 ml ether, washed 3 times with 250 ml water, the organic phase is dried over MgSO$_4$ and the solvent is removed. 18.3 g (80%) of a brown oil are obtained. Elemental analysis % calculated C, H, N: 61.8, 10.1, 6.9; found: 61.3, 10.0, 6.7.

EXAMPLE A3

Preparation of 2-N,N-Dioctyl-ammoniummethyl-2-acrylonitrile, Compound 103

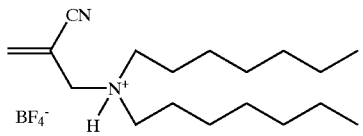

14 g (45.6 mmol) of the compound of example A1 are dissolved in 50 ml water and 50 ml methanol (yellow suspension). 4.5 g of a 35% HCl solution in water are added and the mixture is poured to a solution of 10.02 g sodium tetrafluoroborate in 100 ml water. The title product is isolated as described in example A2. 13.1 g (73%) are obtained.

NMR (CDCl$_3$): 0.85 ppm (t, 6H), 1.24 ppm (m, 6H) 1.69 ppm (m, 4H), 3.03 ppm (m, 4H), 3.85 ppm (s, 2H), 6.42 and 6.51 ppm (2s, 2H, olefinic).

EXAMPLE A4

Preparation of 2-N,N-Dimethyl-aminomethyl 2-Acrylonitrile, Compound 104

The title compound is prepared in analogy to example A1. Yield 70% of a slightly brown oil. Elemental analysis % calculated C, H, N: 61.2, 10.3, 28.5; % found: 63.0, 9.2, 25.3.

EXAMPLE A5

Preparation of 2-N,N-Dimethyl-ammoniummethyl 2-Acrylonitrile, Compound 105

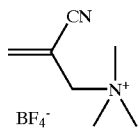

The title compound is prepared starting from the compound of example A4 in analogy to example A2. Yield 39.6% white solid.

Elemental analysis % calculated C, H, N: 39.7, 6.2, 13.2; % found: 39.8, 6.2, 13.1.

Ammonium Salts with Y=COOEt

EXAMPLE A6

Preparation of 2-N,N-Dimethyl-aminomethyl 2-Acrylocarboxyethyl, Compound 106

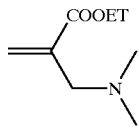

Compound 106 is prepared in analogy to compound 101. Yield 99%. Elemental analysis % calculated C, H, N: 61.1, 9.6, 8.9; % found: 60.7, 9.5, 9.3.

EXAMPLE A7

Preparation of 2-N,N-Dioctyl-aminomethyl 2-Acrylocarboxyethyl, Compound 107

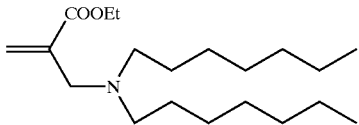

Compound 107 is prepared in analogy to compound 106. Yield 99%. Elemental analysis % calculated C, H, N: 74.7, 12.3, 4.0; % found: 74.6, 12.4, 9.3.

EXAMPLE A8

Preparation of Compound 108

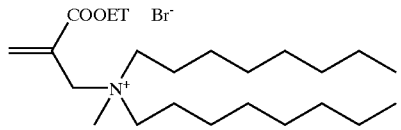

20 g N,N-Dioctylmethylamine (78.3 mmol) in 100 ml methylethyl ketone (MEK) are heated to 60° C. under nitrogen atmosphere. 15.1 g (78.3 mmol) α-bromomethyl ethylacrylate are dropwise added. After 4 h stirring the solvent is removed and 99% product is obtained. Elemental analysis % calculated C, H, N: 61.59, 10.34, 3.12; % found: 61.02, 10.34, 2.94.

EXAMPLE A9

Preparation of Compound 109

15.7 g compound 108 in 400 ml water and 400 ml methanol are dropped into a solution of 12.9 g KPF$_6$ in 400 ml water. The slightly yellow mixture is concentrated, 50 ml ether are added, the organic phase is separated and washed with 50 ml water. After drying over MgSO$_4$ and evaporation of solvent a yellow wax is obtained. Yield 13.5 g (75%). Elemental analysis % calculated C, H, N: 53.79, 9.03, 2.73; % found: 53.61, 9.17, 2.76.

EXAMPLE A10

Preparation of Compound 110

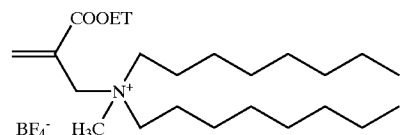

8 g of compound 107 in 250 ml CH$_2$Cl$_2$ are mixed with 3.04 g trimethyloxonium tetrafluoroborate in two portions. After stirring for 12 h the title compound is isolated in 93% yield. Elemental analysis % calculated C, H, N: 60.66, 10.18, 3.08; % found: 61.08, 10.38, 3.16.

EXAMPLE A11

Preparation of Compound 111

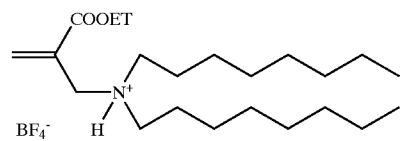

7.7 g of compound 107 in 30 ml water are mixed with 3.5 ml HBF$_4$ (50% solution in water). After one hour stirring at room temperature the mixture is extracted two times with ether and the organic phase is washed with water and dried over MgSO$_4$. After evaporation of the solvent 4.8 g of an orange oil are obtained (54.5% yield). Elemental analysis % calculated C, H, N: 59.86, 10.05, 3.17; % found: 59.90, 10.05, 3.23.

EXAMPLE A12

Preparation of Compound 112

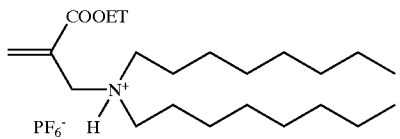

Compound 112 is prepared in analogy to compound 111, using KPF$_6$. Elemental analysis % calculated C, H, N: 52.90, 8.88, 2.80; % found: 53.08, 8.83, 2.83.

EXAMPLE A13

Preparation of Compound 113

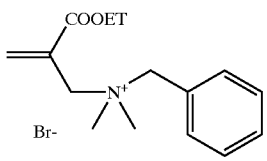

6.1 g (38.8 mmol) of compound 106, 13.3 g benzyl bromide (77.6 mmol) in 75 ml methyl ethyl ketone (MEK) are stirred for 2 h at 60° C. The resulting mixture is poured into 400 ml ether, filtrated and dried. 9.96 g, 78% yield of the title compound are obtained.

NMR (CDCl$_3$): 1.29 ppm (t, 3H), 3.12 ppm (s, 6H), 4.21 ppm (q, 2H), 4.79 ppm (s, 2H), 5.04 ppm (s, 2H), 6.91 and 6.92 ppm (2xs, 2H olefinic), 7.43 ppm (m, 3H), 7.64 ppm (m, 2H).

EXAMPLE A14

Preparation of Compound 114

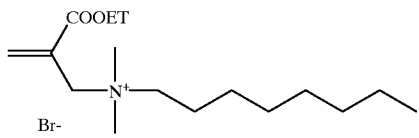

N,N-octyldimethylamine and α-bromomethyl ethylacrylate are mixed in equimolar amounts. Temperature raises up to 60° C. After cooling to room temperature the product is washed with ether and dried under vacuum. Yield 41%. Elemental analysis % calculated C, H, N: 54.85, 9.21, 4.00; % found: 54.55, 9.27, 3.99.

EXAMPLE A15

Preparation of Compound 115

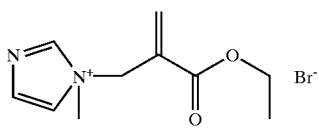

5 g imidazole (60.9 mmol) in 40 ml MEK are heated to 60° C. 11.75 g α-bromomethyl ethyl acrylate are added over 10 min dropwise. After 3 h at 60° C. the mixture is cooled down, poured into 300 ml water and washed three times with 150 ml ether. The title compound is obtained in 74% yield.

EXAMPLE A16

Preparation of Compound 116

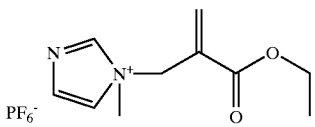

Before isolation of compound 115, the water phase is dropwise added to 22.4 g KPF$_6$ in 400 ml water. The title product precipitates partially and is washed four times with 250 ml CH$_2$Cl$_2$. The organic phases are dried over MgSO$_4$ and the solvent is evaporated. 15.3 g (74%) are obtained. Elemental analysis % calculated C, H, N: 35.31, 4.44, 8.23; % found: 34.96, 4.31, 8.30.

EXAMPLE A17

Preparation of Compound 117

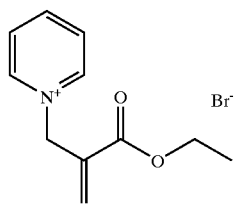

A solution of 7.9 g pyridine in 20 ml methyl ethyl ketone (MEK) is heated to 60° C. and 1.93 g α-bromomethyl ethylacrylate are added dropwise in 30 min. The mixture is stirred at 60° C. for 1.5 h. After cooling to room temperature the mixture is poured on 200 ml water and the organic phase is extracted two times with water. The product is obtained in 95% yield.

EXAMPLE A18

Preparation of Compound 118

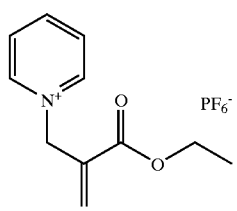

2.72 g of compound 117 in 50 ml water are added to a solution of 3.68 g KPF$_6$ in 20 ml water. After 1 h the solution is filtered and the solid residue is washed with water (2×50 ml). After drying under vacuum 3.19 g of a wax are obtained (95% yield).

NMR (CDCl$_3$): 1.05 ppm (t, 3H, COOC—CH$_3$), 3.97 ppm (q, 2H, COOCH$_2$—Me), 5.25 ppm (s, 2H, allylics), 5.28 und 5.46 (2 s, olefinics), 7.85 (t, 2H, H-3 und H-5 py), 8,34 (t, H-4-py), 8.76 ppm (d, H-2 und H-6 py).

Ammonium Salts with Y=Phenyl

α-bromomethyl-styrene is prepared according to Journal of Organic Chemistry, 1957, 22 113 or Journal of American Chemical Society, 1054, 76, 2705.

EXAMPLE A19

Preparation of Compound 119

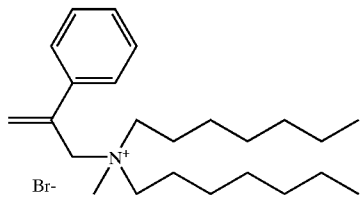

20 g dioctylmethylamine in 100 ml MEK are heated to 60° C. 1 equivalent α-bromomethyl styrene is dropwise added in 10 min. The mixture is stirred 5 h at 60° C. and then cooled to room temperature. The mixture is poured into 800 ml ether and the product precipitates. After filtration 30.4 g (86%) of a solid are obtained. Elemental analysis % calculated C, H, N: 69.0, 10.2, 3.1; % found: 69.1, 10.4, 3.0.

EXAMPLE A20

Preparation of Compound 120

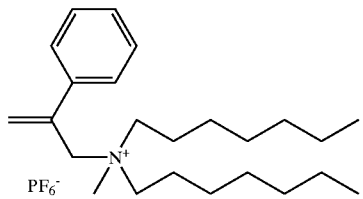

30.4 g of compound 119 (67.2 mmol) in 500 ml water and 500 ml methanol are added dropwise to a solution of 24.7 g Potassium hexafluorophosphate in 800 ml water. The title compound precipitates. After filtration and drying 31.9 g (91% yield) are obtained. Elemental analysis % calculated C, H, N: 60.3, 9.0, 2.7; % found: 60.3, 9.0, 2.6.

EXAMPLE A21 to A25

Preparation of Compounds 121, 122, 123, 124 and 125.

All compounds are prepared in analogy to compound 120 of example A20.

compound 121

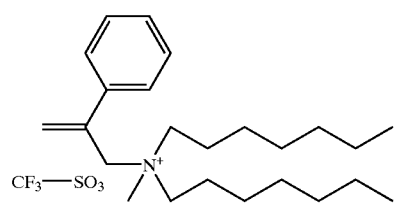

Potassium trifluoromethansulfonate instead of potassium hexafluorophosphate. Elemental analysis % calculated C, H, N: 62.1, 8.9, 2.7; % found: 62.5, 9.1, 2.6.

compound 122

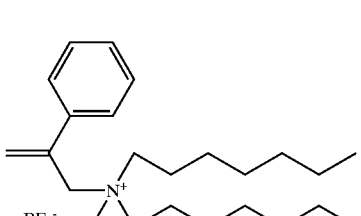

Sodium para-toluenesulfonate instead of potasium hexafluorophosphate. Elemental analysis % calculated C, H, N: 72.9, 9.8, 2.6; % found: 72.9, 9.7, 2.6.

compound 123

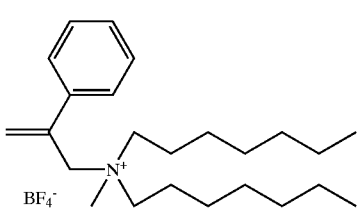

Sodium tetraphenylborate instead of potassium hexafluorophosphate. Elemental analysis % calculated C, H, N: 86.8, 9.6, 2.0; % found: 86.7, 9.4, 2.0.

compound 124

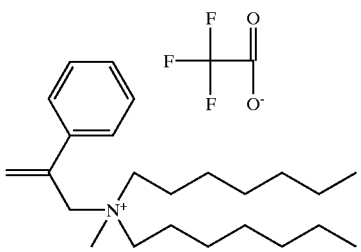

Sodium tetrafluoroborate instead of potassium hexafluorophosphate. Elemental analysis % calculated C, H, N: 68.0, 10.1, 3.1; % found: 67.9, 10.0, 3.1.

compound 125

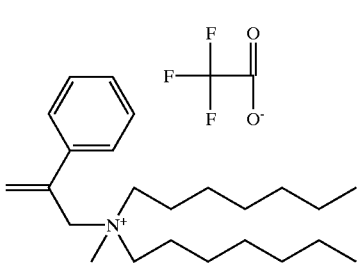

Trifluoroacetic acid sodium salt instead of potasium hexafluorophosphate. Elemental analysis % calculated C, H, N: 69.25, 9.55, 2.88; % found: 69.15, 9.48, 2.96.

EXAMPLE A26

Preparation of Compound 126

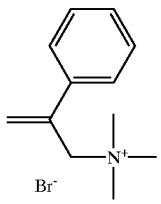

The title compound is prepared in analogy to compound 119. Yield 91% white solid.

NMR (CDCl$_3$): 3.3 ppm (s, 9H), 5.04 ppm (s, 2H), 5.82 and 6.03 ppm (2s, 2H, olefinic), 7.3–7.56 ppm (m, 5H, styrenic).

EXAMPLE A27

Preparation of Compound 127

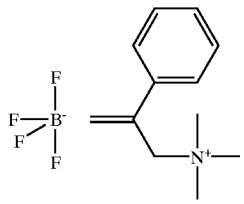

To a solution of compound 126 (6.14g, 55.8 mmol) in 60 CH$_2$Cl$_2$, 7.5 g trimethyloxonium tetrafluoroborate are added in portions. The mixture is stirred for 16 h, filtered and washed with 4 portions of water. After recrystallization from 100 ml ethanol 3.4 g (30%) of a white solid are obtained. Elemental analysis % calculated C, H, N: 39.66, 6.18, 13.21; % found: 39.59, 6.11, 13.24.

EXAMPLE A28

Preparation of Compound 128

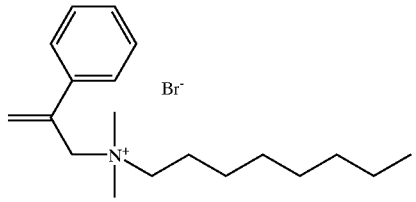

3.15 g dimethyloctylamine (20 mmol) in 20 ml MEK are heated to 60° C. 4.9 g α-bromomethyl-styrene are dropwise added in 30 min. After 2 h stirring the mixture is cooled to room temperature and poured into 400 ml ether. 6.72 g of a white oil are obtained (94.8%). Elemental analysis % calculated C, H, N: 64.4, 9.1, 3.95; % found: 64.12, 9.01, 3.97.

NMR (CDCl$_3$): 0.86 ppm (t, 3H), 1–1,35 ppm (m, 13H), 1.54 ppm (m, 2H), 3.28 ppm (s, 6H), 3.3–3.4 (m, 2H), 5.05 ppm (s, 2H), 5.84 ppm (s, 1H), 6.12 ppm (s, 1H), 7.36–7.57 ppm (m, 5H).

EXAMPLE A29

Preparation of Compound 129

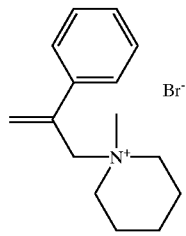

3.8 ml N-methylpiperidine (2.51 g, 25.37 mmol) in 100 ml MEK are heated to 60° C. 5 g α-bromomethyl-styrene are added dropwise in 5 min. After 8 h the mixture is cooled to room temperature and poured into 600 ml ether. After washing and drying 5.47 g (73%) of a white solid are obtained. Elemental analysis % calculated C, H, N: 60.81, 7.49, 4.72; % found: 60.68, 7.70, 4.80.

EXAMPLE A30

Preparation of Compound 130

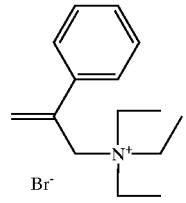

The title compound is prepared in analogy to example A19. 14.46g (88%) of a white solid are obtained.

NMR (CDCl$_3$): 1.29 ppm (t, 9H), 3.32 ppm (q, 6H), 4.68 ppm (s, 2H), 5.73 and 5.9 ppm (2s, 2H, olefinic), 7.32–7.45 ppm (m, 5H, styrenic).

EXAMPLE A31

Preparation of Compound 131

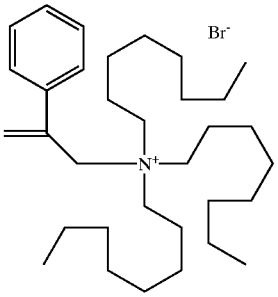

The title compound is prepared in analogy to example A19. Elemental analysis % calculated C, H, N: 71.97, 10.98, 2.54; % found: 70.44, 10.55, 2.37.

EXAMPLE A32

Preparation of Compound 132

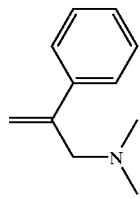

108 ml of a 33% solution of dimethylamine in ethanol are diluted with 250 ml MEK and heated to 60° C. 46.36 g (0.2 mol) α-bromomethylstyrene are added dropwise in 30 min. The mixture is stirred for 1 h at 60° C. and cooled down to room temperature. Solvent is evaporated, the residue redissolved in ethylacetate and purified on silica gel. 27.8 g (86%) of a yellowish oil are obtained.

EXAMPLE A33

Preparation of Compound 133

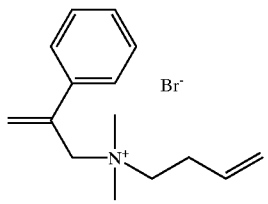

8.6 g (50 mmol) of compound 132 in 50 ml MEK are heated to 60° C. 5.1 ml (6.8 g, 50 mmol) 4-brom-1-butene are added in 30 min. The mixture is poured in 200 ml ether. The ether phase is removed, the residue is washed with ether and concentrated. After drying under vacuum 11.92 g of a resinous product are obtained (80.4%)

NMR (CDCl$_3$): 2.47 ppm (m, 2H, allylic), 3.25 ppm (s, 6H, CH$_3$), 3.44 ppm (m, 2H), 5.02 ppm (s, 2H), 5.8–4.98 ppm (3H, term. olefinic), 5.79 and 6.06 (2s, 2H, olefinic), 7.3–7.54 ppm (m, 5H, styrenic).

EXAMPLE A34

Preparation of Compound 134

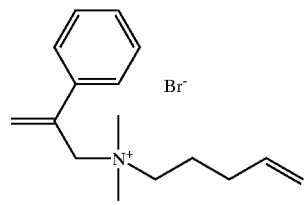

The title compound is prepared in analogy to compound 133 of example A33, with 4.7 ml (40 mmol) of 4-bromo-1-pentene and 6.45 g of compound 132. Yield 31.6%. Elemental analysis % calculated C, H, N: 61.94, 7.80, 4.51; % found: 61.84, 7.87, 4.43.

EXAMPLE A35

Preparation of Compound 135

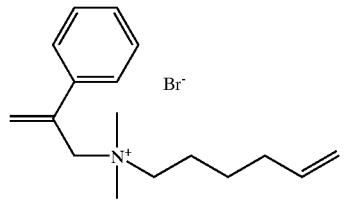

The title compound is prepared in analogy to compound 133 of example A33.

NMR (CDCl$_3$): 1.17 ppm (m, 2H), 1.63 ppm (m, 2H), 1.96 ppm (m, 2H), 3.27 ppm (s, 6H), 4.98 ppm (s, 2H), 4.9–5.67 ppm (m, 3H, terminal olefin), 5,8 and 6.06 ppm (2s, 2H) 7.32–7.52 ppm (m, 5H, styrenic).

EXAMPLE A36

Preparation of Compound 136

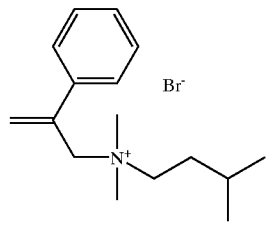

The title compound is prepared in analogy to compound 133 of example A33, with 6.3 ml (50 mmol) 1-Bromo-3-Methyl-butane give a yield of 42.3%

NMR (CDCl$_3$): 0.76 ppm (d, 6H, J=6.5 Hz), 1.29–1.53 ppm (m, 3H), 3,23 ppm (s, 6H), 3.345 ppm (m, 2H), 4.98 ppm (s, 2H), 5.78 and 6.07 ppm (2s, 2H, olefinic), 7.32–7.51 ppm (m, 5H, styrenic).

EXAMPLE A37

Preparation of Compound 137

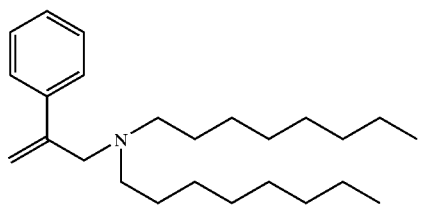

11.46 g (50 mmol) α-bromomethyl-styrene is added dropwise at 60° C. in 30 min to a solution of 36.17 g N,N-dioctylamine in 200 ml MEK. The solution is stirred at 60° C. for 8 h and cooled down to room temperature. The mixture is poured in 200 ml toluene, the organic phase is washed three times with 250 ml water dried over MgSO$_4$ and concentrated. 24.1 g of the title product are obtained and used for the next reaction step.

EXAMPLE A38

Preparation of Compound 138

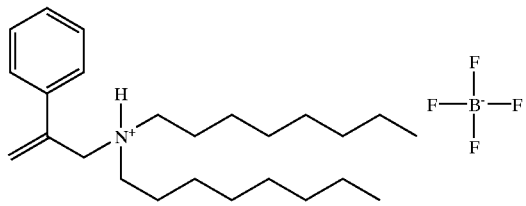

12.47 g of compound 137 in 50 ml water and 100 ml methanol are treated with 3.11 g of a 35% HCl solution in water and a solution of 6.95 g $NaBF_4$ in 70 ml water is dropwise added. After 25 min methanol is removed and a brown emulsion is obtained, 100 ml ether are added and the organic phase is dried over $MgSO_4$. After evaporation of the solvent 9 g of an oil are obtained (57%).

NMR ($CDCl_3$): 0.87 ppm (t, 6H, $C_8$-termini), 1.22 ppm (m, 20H), 1.4 ppm (m, 4 H), 2.38 ppm (t, 4H, $N^+CH_2$), 3.37 (s, 3H, N+$CH_3$), 5.25 und 5.39 ppm (2s, 2H, olefins), 7.2–7.5 ppm (m, 5H, styrenic).

EXAMPLE A39

Preparation of Compound 139

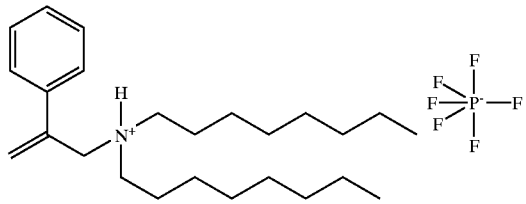

4.83 g of compound 137 are dissolved in 100 ml water and 50 ml MeOH. 1.72 ml hexafluoro acid (65% in water) are added in 10 min. The mixture is stirred for 6 h at room temperature, several times extracted with ether, the organic phase dried over $MgSO_4$ and the solvent evaporated. 4.07 g (60%) of the title compound are obtained. Elemental analysis % calculated C, H, N: 59.65, 8.81, 2.78; % found: 59.73, 8.48, 2.76.

EXAMPLE A40

Preparation of Compound 140

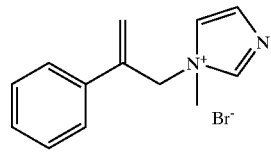

5 g N-methylimidazole in 40 ml MEK are heated to 60° C. and 12 g α-bromomethyl-styrene are added in 10 min. After 2,5 h stirring, the mixture is poured into 400 ml water, and extracted with ether. The water phase is directly used for the next reaction step.

EXAMPLE A41

Preparation of Compound 141

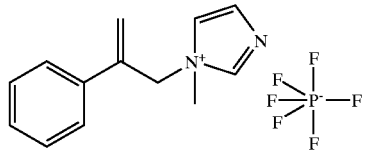

Approximately 17 g of compound 140 in 400 ml water are slowly added to a solution of 22.4 (2 Aeq.) potasium hexafluorophosphate in 200 ml water. After 1.5 h the suspension is filtered, washed and dried. Elemental analysis % calculated C, H, N: 45.36, 4.39, 8.14; % found: 45.57, 4.50, 8.16.

EXAMPLE A42

Preparation of Compound 142

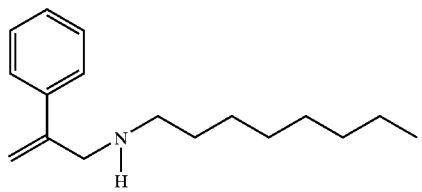

34.8 ml octylamin in 200 ml ether are heated to 40° C. and 16.04 g α-bromomethyl-styrene are added dropwise in 10 min. The mixture is stirred for 8 h at room temperature, filtered, dried and chromatographically purified. 6.36 g (37%) of the title compound are obtained. Elemental analysis % calculated C, H, N: 83.20, 11.09, 5.71; % found: 83.24, 11.29, 5.77.

EXAMPLE A43

Preparation of Compound 143

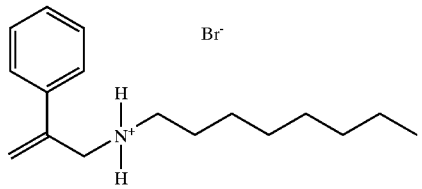

To 5 g of compound 142 in 200 ml water the equivalent amount of HBr is added. The product is filtered off. Elemental analysis % calculated C, H, N: 62.57, 8.65, 4.29; % found: 62.67, 8.60, 4.39.

EXAMPLE A44

Preparation of Compound 144

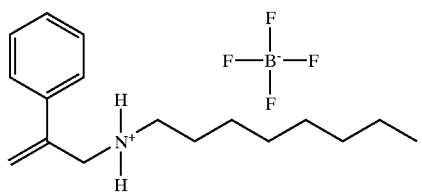

0.75 g of compound 143 in 10 ml water and 30 ml MeOH are added to a solution of 0.5 g NaBF₄ in 10 ml water. After 1 h at room temperature the mixture is extracted with ether, the organic phase is washed with water, dried over MgSO₄ and the solvent evaporated. After purification by chromatography 200 mg product (26%) are obtained.

NMR (CDCl₃): 085 ppm (s, 3H), 1.2 ppm (broad s, 10H), 1.54 ppm (s, 2H), 2.77 ppm (m, 2H), 3.94 ppm (s, 2H), 4.39 ppm (s, 2H) 5.40 and 5.55 ppm (2s, 2H, olefinic) 7.2–7.4 ppm (m, 5H, styrenic).

EXAMPLE A45

Preparation of Compound 145

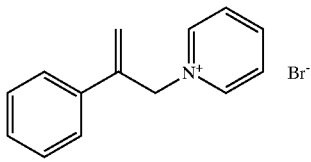

3.96 g pyridine in 80 ml MEK are heated to 60° C. 11.73 g α-bromomethyl-styrene are added in 15 min and the solution stirred for 8 h at 60° C. After cooling to room temperature, filtration and washing with MEK, 85 g (42.4%) of the title compound are obtained. Elemental analysis % calculated C, H, N: 60.89, 5.10, 5.07; % found: 60.95, 5.1, 5.11.

EXAMPLE A46

Preparation of Compound 146

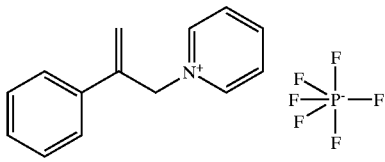

5.52 g of compound 145 in 100 ml water are added dropwise to a solution of KPF₆ in 20 ml water. The solid product is filtered off, washed and dried. 3.6 g (53%) of the title compound are obtained. Elemental analysis % calculated C, H, N: 49.28, 4.14, 4.10; % found: 49.30, 4.21, 4.06.

EXAMPLE A47

Preparation of Compound 147

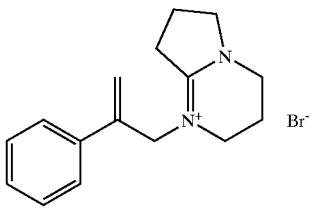

4.97 g diazabicyclononane and 9.17 g α-bromomethyl-styrene in 80 ml toluene are mixed and stirred for 18 h at room temperature. The solvent is evaporated and the residue is extracted with ether. After evaporation of the solvent 10.9 g (85%) of the title compound are obtained.

NMR (CDCl₃): 2.05–2.23 ppm (m, 4H), 3.18 ppm (t, 2H), 3.52 ppm (m, 4H), 3.81 ppm (t, 2H), 4.48 ppm (s, 2H), 5.23 and 5.49 ppm (2s, 2H, olefinic) 7.29 ppm (m, 5H, styrenic).

EXAMPLE A48

Preparation of Compound 148

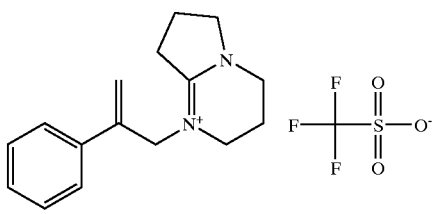

6.43 g of compound 147 in 150 ml water are added dropwise in 15 min to a solution of 7.53 g potasium trifluormethanesulfonate in 250 ml water. The mixture is stirred for 90 min at room temperature, extracted with ethylacetate, the organic phase is washed several times with water and dried over MgSO₄. After evaporation of the solvent 3.96 g (50%) of the title compound are obtained. Elemental analysis % calculated C, H, N: 52.30, 5.42, 7.18; % found: 51.77, 5.40, 7.21.

EXAMPLE A49

Preparation of Compound 149

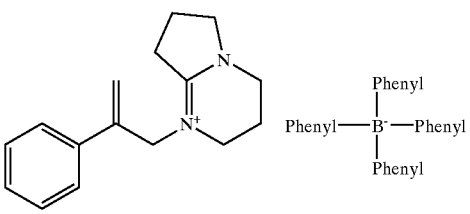

1.4 g of compound 147 in 150 ml water are added to a solution of 3 g sodium tetraphenylborate in 150 ml water in 15 min. After 1 h stirring at room temperature, the mixture is extracted with CH₂Cl₂, the organic phase is washed with water and the solvent is evaporated. The solid residue is extracted with MeOH and the solid filtered off. 1.59 g (65%) of the title compound are obtained.

NMR (CDCl₃): 1.27 ppm (m, 2H), 1.42 ppm (m, 2H), 1.83 ppm (m, 2H), 2.37 ppm (m, 2H), 2.57 ppm (m, 2H), 2.8 ppm (m, 2H), 3.54 ppm (s, 2H), 4.83 und 5.34 ppm (2s, 2H, olefinic), 5.81, 6.95, 7.11, 7.23, 7.32 und 7.4 ppm (m, 25H, styrenic+tetraphenylborate).

EXAMPLE A50

Preparation of Compound 150

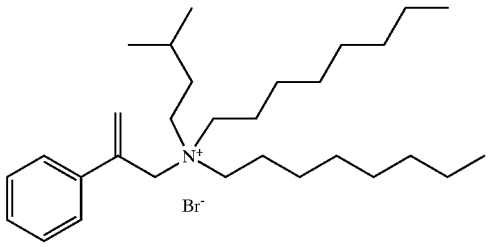

The title compound is prepared in analogy to compound 119, with dihexyl-(3-methyl-butyl)-amine. Yield 75% white solid.

¹H-NMR (300 MHz, CDCl₃): 0.75–0.85 ppm (m, 12H), 0.93–1.08 ppm (m, 4H), 1.09–1.27 ppm (m, 16H), 1.30–1.42 ppm (m, 1H), 1.42–1.66 ppm (m, 6H), 3.04–3.21 ppm (m, 6H), 4.78 ppm (s, 2H), 5.70 and 5.83 ppm (2s, 2H, olefinic), 7.25–7.46 (m, 5H, styrenic).

¹³C-NMR (75 MHz, CDCl₃): 14.3, 22.7, 22.8, 26.4, 26.5, 29.3, 30.8, 31.8, 58.4, 59.4, 62.8, 127.1, 129.1, 129.5, 129.6, 138.5, 140.1.

EXAMPLE A51

Preparation of Compound 151

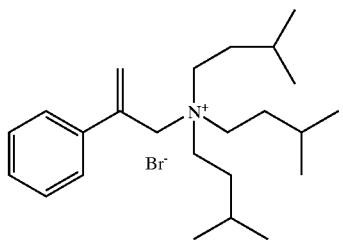

The title compound is prepared in analogy to compound 119, with triisopentylamine. Yield 79% white solid.

¹H-NMR (300 MHz, CDCl₃): 0.85 ppm (d, J=6.6 Hz, 18H), 1.30–1.44 ppm (m, 6H), 1.47–1.58 ppm (m, 6H), 3.15–3.25 ppm (m, 6H), 4.81 ppm (s, 2H), 5.74 and 5.90 ppm (2s, 2H, olefinic), 7.30–7.50 ppm (m, 5H, styrenic).

¹³C-NMR (75 MHz, CDCl₃): 22.7, 26.6, 30.9, 58.6, 63.0, 127.1, 129.2, 129.5, 129.8, 138.5, 140.2. ESI-TOF-MS: 344.4 ([M-Br]⁺), 769.8 ([2M-Br]⁺).

EXAMPLE A52

Preparation of Compound 152

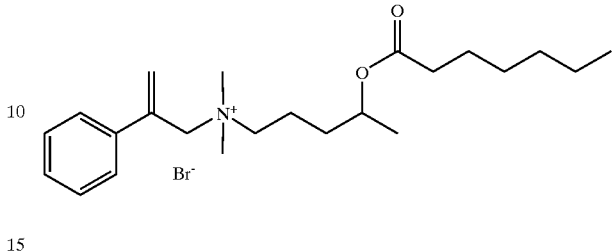

The title compound is prepared in analogy to compound 119, with heptanoic acid 4-dimethylamino-1-methyl-butyl ester. Yield 77% beige solid.

¹H-NMR (300 MHz, CDCl₃): 0.82–0.92 ppm (m, 3H), 1.17 ppm (d, J=6.3 Hz, 3H), 1.21–1.85 ppm (m, 12H), 2.22–2.31 ppm (m, 2H), 3.24 ppm (s, 3H), 3.27 ppm (s, 3H), 3.41–3.54 ppm (m, 2H), 4.73–4.85 ppm (m, 1H), 5.06 ppm (s, 2H), 5.85 and 6.11 ppm (2s, 2H, olefinic), 7.31–7.48 ppm (m, 3H, styrenic), 7.52–7.60 ppm (m, 2H, styrenic).

¹³C-NMR (75 MHz, CDCl₃): 14.3, 19.5, 20.4, 22.8, 25.3, 29.1, 31.7, 32.6, 34.9, 51.4, 64.2, 67.0, 127.0, 129.2, 129.7, 129.9, 138.2, 139.5, 173.8. ESI-TOF-MS: 360.3 ([M-Br]⁺), 801.6 ([2M-Br]+).

EXAMPLE A53

Preparation of Compound 153

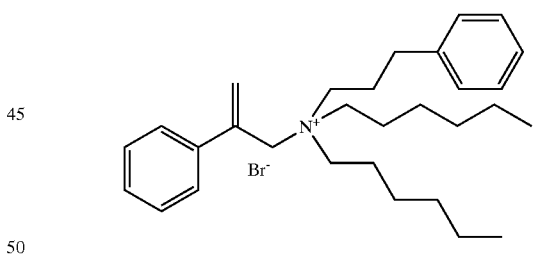

The title compound is prepared in analogy to compound 119, with dihexyl-(3-phenyl-propyl)-amine. Yield 52% white solid.

¹H-NMR (300 MHz, CDCl₃): 0.75–0.84 ppm (m, 6H), 0.92–1.23 ppm (m, 12H), 1.40–1.58 (m, 4H), 1.97–2.10 ppm (m, 2H), 2.47–2.56 (m, 2H), 3.16–3.26 ppm (m, 6H), 4.74 ppm (s, 2H), 5.64 and 5.77 ppm (2s, 2H, olefinic), 7.08–7.42 ppm (m, 10H, styrenic).

¹³C-NMR (75 MHz, CDCl₃): 15.0, 23.5, 25.3, 26.9, 32.2, 33.1, 59.5, 60.4, 63.8, 127.8, 129.7, 129.9, 130.0, 130.4, 130.6, 139.1, 140.5, 140.9. ESI-TOF-MS: 420.5 ([M-Br]⁺).

Phosphonium Salts

EXAMPLE A54

Preparation of Compound 154

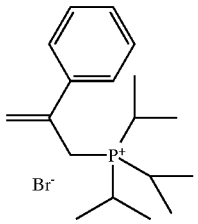

6.4 g tris-isopropyl phosphine (0.04 mol) are added dropwise to 7.5 g (0.04 mol) α-bromo-methyl-styrene in tetrahydrofurane (THF). The white solid which immediately precipitates is filtered off and dried. 13 g (100%) of the title compound are obtained. Elemental analysis % calculated C, H: 60.51, 8.46% found: 60.49, 8.56.

EXAMPLE A55

Preparation of Compound 155

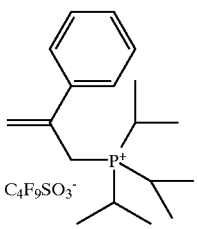

6.08 g of compound 154 (17 mmol) in 50 ml water are added dropwise to a solution of 11.5 g (34 mmol) potassium-nonafluoro-1-butanesulfonate in 50 ml water. The white solid which immediately precipitates is filtered off and dried. 8.05 g (82%) of the title compound are obtained. Elemental analysis % calculated C, H,: 45.84%, 5.25% found: 45.86%, 5.22%.

EXAMPLE A56

Preparation of Compound 156

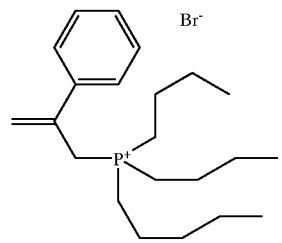

The title compound is prepared in analogy to compound 155 in 77.5% yield. Elemental analysis % calculated C, H: 63.15, 9.08 found: 63.04, 8.90.

EXAMPLE A57

Preparation of Compound 157

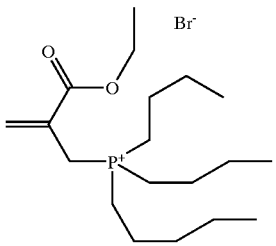

To a solution of 6.6 g (34.1 mmol) α-bromomethyl-carboxylate in 50 ml tetrahydrofurane 6.9 g tributylphosphine (34.1 mmol) are added under argon atmosphere. The title compound precipitates, is washed with tetrahydrofurane and dried. 94.1% are obtained. NMR (CDCl$_3$): 0.97 ppm (m, 9H), 1.34 ppm (t, 3H), 1.53 ppm (m, 12H), 2.43 ppm (m, 6H), 3.9 and 3.96 ppm (2s, 2H) 4.24 ppm (q, 2H), 6.55 und 6.67 ppm (2s, 2H olefinic), 6.78–6.80 ppm (2s, 2H, olefinic).

Dienes

EXAMPLE A58

Preparation of Compound 158

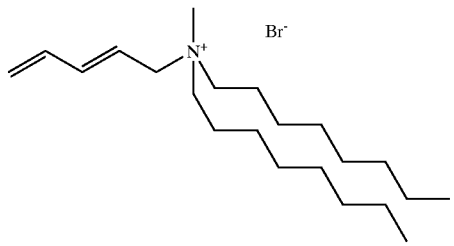

The bromide is prepared according to Jiang S., Viehe H., Oger N. and Charmot P., Macromol. Chem. Phys. 1995, 196, 2349.

5.11 g dioctylamine (20 mmol) and 2.94 g 5-bromo-1,3-pentadiene in 30 ml methyl ethyl ketone are heated to 60° C. After evaporation of the solvent 0.38 g of the title compound are obtained as a white solid, which is directly used for the next reaction step. Elemental analysis % calculated C, H, N: 65.65, 11.02, 3.48 found: 66.04, 11.11, 3.40.

EXAMPLE A59

Preparation of Compound 159

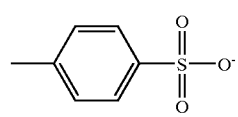

-continued

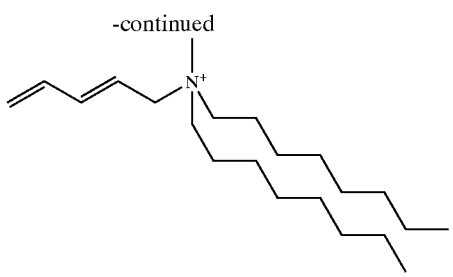

2.27 g of compound 158 (6 mmol) in 25 ml water are mixed with 7.77 g toluene-4-sulfonic acid sodium salt in 25 ml water. After 1 h stirring at room temperature 50 ml ether are added, the water phase is additionally extracted twice with 50 ml ether, the organic phases are combined, dried over MgSO$_4$ and the solvent is evaporated. 0.53 g of the title compound (86%) are obtained. Elemental analysis % calculated C, H, N, S: 70.54, 10.41, 2.84, 6.49%; found: 70.56, 10.74, 2.83, 5.93.

EXAMPLE A60

Preparation of Compound 160

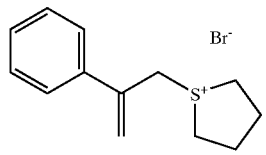

To a solution of 2.31 g (10 mmol) α-bromomethyl-styrene in 10 ml ether, 0.9 ml tetrahydrothiophen are added dropwise in 30 min. The title compound precipitates and is washed with ether.

Elemental analysis % calculated C, H: 54.74, 6.01; % found: 54.92, 5.96.

EXAMPLE A61

Preparation of Compound 161

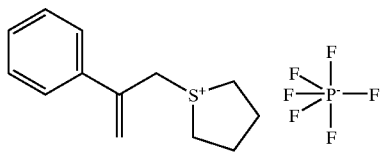

Compound 160 of example 60 is dissolved in water together with KPF$_6$. The title compound precipitates in a yield of 86%.

NMR (CDCl$_3$): 2.35 ppm (m, AA'BB', 4H), 3.48 ppm (m, AA'BB', 4H), 4.51 ppm (s, 2H), 5.59 und 5.84 ppm (2s, olefinic, 2H), 7.41 ppm (m, 3H), 7.56 ppm (m, 2H).

B) APPLICATION EXAMPLES

Photochemical Polymerization of Methyl Acrylate
20% in Ethyl Acetate
General Procedure Polymerization without addition fragmentation agents. 90 g of a solution containing 18 g methyl acrylate, 70.91 g ethyl acetate and 85.4 mg (0.42 mmol) Irgacure 184 is irradiated under inert gas (argon) for 48 minutes at 25° C. with a 6 inch Fusion D-bulb in a 26 cm$^2$ reactor as described in European Patent Application No. 97102677.8 setup A. The distance between the lamp and the reactor window in set-up (A) (no casserole) is fixed at 26 cm. The solution is stabilized with 25 ppm hydroxymethyl hydroquinone. After isolation of the polymer the solvent is evaporated to constant polymer weight.

Irgacure 184

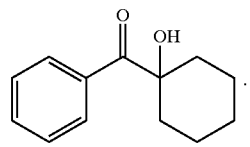

The above procedure is carried out in the same manner, and various addition fragmentation agents are added in different amounts.

Mn and Mw are determined by gel permeation chromatography (GPC).

The results are given in Table 1

TABLE 1

| No. | Compound No. | amount | | Mn | PD |
|---|---|---|---|---|---|
| B1 | none | 0 | | 22100 | 2.9 |
| B2 | 120 | 220 | mg, 0.2 mol % | 13774 | 1.9 |
| B3 | 120 | 540 | mg, 0.5 mol % | 8624 | 1.8 |
| B4 | 120 | 1080 | mg, 1 mol % | 6096 | 1.6 |
| B5 | 119 | 189.2 | mg, 0.2 mol % | 13650 | 1.9 |
| B6 | 119 | 473.1 | mg, 0.5 mol % | 11254 | 1.8 |
| B7 | 119 | 946.2 | mg, 1 mol % | 11550 | 1.8 |
| B8 | 109 | 214.8 | mg, 0.2 mol % | 16883 | 1.5 |
| B9 | 109 | 536.9 | mg, 0.5 mol % | 8672 | 1.8 |
| B10 | 109 | 1073.8 | mg, 1 mol % | 6684 | 2.0 |
| B11 | 111 | 184.6 | mg, 0.2 mol % | 13317 | 1.9 |
| B12 | 111 | 461.4 | mg, 0.5 mol % | 9981 | 1.9 |
| B13 | 111 | 922.9 | mg, 1 mol % | 6386 | 1.7 |
| B14 | 121 | 583 | mg, 0.5 mol % | 8443 | 1.8, $C_x$ = 1.24 |
| B15 | 122 | 568.6 | mg, 0.5 mol % | 7439 | 1.9, $C_x$ = 1.52 |
| B16 | 123 | 723.3 | mg, 0.5 mol % | 11620 | 1.6, $C_x$ = 0.68 |
| B17 | 124 | 480.3 | mg, 0.5 mol % | 7406 | 1.9, $C_x$ = 1.53 |
| B18 | 125 | 507.7 | mg, 0.5 mol % | 7748 | 1.42, $C_x$ = 1.42 |

PD = Polydispersity, $C_x$ is transfer coefficient

C) APPLICATION EXAMPLES

Thermal Polymerization of Methyl Acrylate

General Description of the Experiments.

Individual stock solutions are prepared as listed below. After addition of various amounts of addition fragmentation agent, the magnetically stirred solutions are heated under inert atmosphere for a given period of time at a given temperature. After the reaction time the solutions are cooled in an ice bath and 25 ppm of stabilizer (hydroquinone) are added. The solvent is then removed under reduced pressure and the polymer analyzed by GPC and NMR. To prevent any undesired reactions, solvents and monomers as well as reactants are purified by usual techniques before use.

EXAMPLE C1

Stock solution: methyl acrylate 51.24 g, ethylacetate 193.57 g, AIBN 182.9 mg Polymerization 16 hours at 60° C.

| solution | compound 119 | Mn | PD |
|---|---|---|---|
| 38.02 g | 0 | 122872 | 2.7 |
| 39.52 g | 48.2 mg | 17801 | 2.0 |
| 39.51 g | 85.8 mg | 11666 | 1.9 |
| 37.93 g | 209.3 mg | 6631 | 1.8 |
| 35.39 g | 425 mg | 3741 | 1.8 |

EXAMPLE C2

Stock solution: methyl acrylate 60.98 g, ethyl acetate 60.52 g, AIBN 113.5 mg Polymerization 16 hours at 60° C.

| Solution | compound 119 | Mn | PD |
|---|---|---|---|
| 19.18 g | 0 | 169647 | 4.6 |
| 19.34 g | 50.8 mg | 38624 | 2.1 |
| 19.52 g | 113.4 mg | 17676 | 2.2 |
| 19.34 g | 258.4 mg | 9062 | 2.1 |
| 19.13 g | 556 mg | 5199 | 2.0 |

EXAMPLE C3

Stock solution: methyl acrylate 37.74 g, ethyl acetate 144 g, AIBN 137.3 mg Polymerization 16 hours at 60° C.

| Solution | compound 120 | Mn | PD |
|---|---|---|---|
| 30.48 g | 0 | 205100 | 2.0 |
| 31.39 g | 74.7 mg | 64100 | 1.7 |
| 31 g | 182.4 mg | 23800 | 1.6 |
| 30.21 g | 363.1 mg | 9300 | 1.7 |
| 32.07 g | 721.7 mg | 4900 | 1.5 |

EXAMPLE C4

Stock solution: methyl acrylate 61.96 g, ethyl acetate 60.32 g, AIBN 115.5 mg Polymerization 16 hours at 60° C.

| solution | compound 120 | Mn | PD |
|---|---|---|---|
| 20.21 g | 0 | 200832 | 4.5 |
| 19.47 g | 60.1 mg | 197136 | 2.9 |
| 19.44 g | 120.8 mg | 60216 | 2.9 |
| 19.16 g | 300.7 mg | 15450 | 2.4 |
| 20.55 g | 603.5 mg | 8701 | 2.1 |

EXAMPLE C5

Stock solution: methyl acrylate 72.19 g, ethyl acetate 73.04 g, AIBN 137.3 mg Polymerization 16 hours at 60° C.

| Solution | compound 120 | Mn | PD |
|---|---|---|---|
| 40.27 g | 0 | 219512 | 3.6 |
| 41.76 g | 4.81 g | 4036 | 1.3 |

EXAMPLE C6

Stock solution: methyl acrylate 50.92 g, ethyl acetate 192 g, AIBN 182.8 mg Polymerization 16 hours at 60° C.

| Solution | compound 124 | Mn | PD |
|---|---|---|---|
| 39.79 g | 0 | 148969 | 2.6 |
| 41.03 g | 45.2 mg | 33445 | 2.4 |
| 40.41 g | 88.3 mg | 17232 | 2.1 |
| 40.17 g | 209.9 mg | 10197 | 2.0 |
| 40.66 g | 444.1 mg | 6252 | 1.8 |

EXAMPLE C7

Stock solution: methyl acrylate 21.52 g, ethyl acetate 18.48 g, AIBN 82.1 mg Polymerization 16 hours at 80° C.

| solution | compound 129 | Mn | PD |
|---|---|---|---|
| 40.08 g | 295.6 mg | 55103 | 2.7 |

EXAMPLE C8

Stock solution: methyl acrylate 43.05 g, ethyl acetate 37.47 g, AIBN 164.2 mg Polymerization 16 hours at 80° C.

| solution | compound 126 | Mn | PD |
|---|---|---|---|
| 43 g | 300 mg | 33755 | 3.1 |

EXAMPLE C8

Stock solution: methyl acrylate 92.26 g, ethyl acetate 92.2 g, AIBN 335.4 mg Polymerization 16 hours at 60° C.; $C_x$ 1.17.

| Solution | compound 130 | Mn | PD |
|---|---|---|---|
| 30.89 g | 0 | 37167 | 4.2 |
| 30.76 g | 515.9 mg | 6302 | 2.1 |

EXAMPLE C9

Stock solution: methyl acrylate 43.05 g, ethyl acetate 36.92 g, AIBN 164.2 mg Polymerization 16 hours at 80° C.

| Solution | compound 130 | Mn | PD |
|---|---|---|---|
| 80 g | 5.97 g | 28488 | 2.4 |

EXAMPLE C10

Stock solution: methyl acrylate 17.22 g, ethyl acetate 0.00 g, AIBN 65.7 mg Polymerization 16 hours at 80° C.

| solution | compound 128 | Mn | PD |
|---|---|---|---|
| above | 2.83 g | 1058 | 2.3 |

EXAMPLE C11

Stock solution: methyl acrylate 43.05 g, ethyl acetate 31.88 g, AIBN 164.2 mg Polymerization 16 hours at 80° C.

| solution | compound 131 | Mn | PD |
|---|---|---|---|
| 75 g | 2.5 g | 3575 | 1.4 |

EXAMPLE C12

Stock solution: methyl acrylate 25.32 g, methyl ethyl ketone 95.45 g, AIBN 94.3 mg Polymerization 16 hours at 60° C.

| solution | compound 136 | Mn | PD |
|---|---|---|---|
| 14.94 g | — | 30605 | 2.5 |
| 21.22 g | 31 mg | 18334 | 2.5 |
| 13.69 g | 59.8 mg | 4177 | 3.1 |
| 8.28 g | 51 mg | 2391 | 2.9 |
| 11.48 g | 152.6 mg | 1503 | 2.7 |

EXAMPLE C13

Stock solution: methyl acrylate 25.32 g, methyl ethyl ketone 95.45 g, AIBN 94.3 mg Polymerization 16 hours at 60° C.

| solution | compound 133 | Mn | PD |
|---|---|---|---|
| 13.67 g | — | 28875 | 2.6 |
| 26.88 g | 43.6 mg | 17094 | 2.3 |
| 17.15 g | 60 mg | 5130 | 2.7 |
| 11.46 g | 90.5 mg | 2613 | 2.2 |
| 13.72 g | 184.8 mg | 1662 | 2.2 |

EXAMPLE C14

Stock solution: methyl acrylate 16.11 g, methyl ethyl ketone 64.45 g, AIBN 61.3 mg Polymerization 16 hours at 60° C.; $C_x$ 2.25.

| solution weight | compound 134 | Mn | PD |
|---|---|---|---|
| 15.82 g | — | 23430 | 3.1 |
| 6.85 g | 101.8 mg | 1717 | 2.1 |

EXAMPLE C15

Stock solution: methyl acrylate 16.11 g, methyl ethyl ketone 64.45 g, AIBN 61.3 mg Polymerization 16 hours at 60° C.; $C_x$ 2.9

| solution | compound 135 | Mn | PD |
|---|---|---|---|
| 15.82 g | — | 23430 | 3.2 |
| 25.76 g | 393.1 mg | 1373 | 2.8 |

EXAMPLE C16

Stock solution: methyl acrylate 61.77 g, ethyl acetate 60.82 g, AIBN 118.6 mg Polymerization 1 hour at 60° C.

| solution weight | compound 110 | Mn | PD |
|---|---|---|---|
| 19.95 g | 0 | 178010 | 4.6 |
| 19.78 g | 75.1 mg | 114303 | 5.8 |
| 20.30 g | 127.2 mg | 44125 | 4.0 |
| 20.26 g | 294 mg | 19322 | 3.1 |
| 20.31 g | 550 mg | 8212 | 3.0 |

EXAMPLE C17

Stock solution: methyl acrylate 62.39 g, ethyl acetate 192 g, AIBN 183.9 mg Polymerization 16 hour at 60° C.; $C_x$ 0.95.

| solution weight | compound 109 | Mn | PD |
|---|---|---|---|
| 40.88 g | 0 | 158288 | 3.8 |
| 42.31 g | 60.8 mg | no GPC | vergessen |
| 37.92 g | 140.9 mg | 29291 | 2.4 |
| 41.12 g | 189.3 mg | 25141 | 2.9 |
| 40.32 g | 341.2 mg | 14401 | 2.9 |

EXAMPLE C18

Stock solution: methyl acrylate 40.13 g, ethyl acetate 39.79 g, AIBN 153 mg Polymerization 16 hour at 60° C.; $C_x$ 1.79.

| solution | compound 114 | Mn | PD |
|---|---|---|---|
| 19.68 g | 0 | 114505 | 5.1 |
| 19.43 g | 242.6 mg | 4579 | 1.8 |
| 20.26 g | 382.6 mg | 3527 | 1.7 |

EXAMPLE C19

Stock solution: methyl acrylate 10.76 g, ethyl acetate 8.85 g, AIBN 164.2 mg Polymerization 16 hour at 60° C.

| solution | compound 114 | Mn | PD |
|---|---|---|---|
| 19.68 g | 1.75 g | 1743 | 2.1 |

EXAMPLE C20

Stock solution: methyl acrylate 51.18 g, ethyl acetate 192 g, AIBN 184.9 mg Polymerization 16 hour at 60° C.

| solution | compound 102 | Mn | PD |
|---|---|---|---|
| 40.42 g | 0 | 138960 | 3.0 |
| 39.66 g | 51.5 mg | 21463 | 1.9 |
| 40.48 g | 144.8 mg | 9143 | 1.9 |
| 39.39 g | 213.2 mg | 5390 | 1.6 |
| 38.03 g | 381.1 mg | 3840 | 1.5 |

EXAMPLE C21

Stock solution: methyl acrylate 48.97 g, ethyl acetate 192 g, AIBN 183.5 mg Polymerization 16 hours at 60° C.

| solution | compound 111 | Mn | PD |
|---|---|---|---|
| 38.97 g | 0 | 104769 | 3.4 |
| 40.19 g | 68.7 mg | 94066 | 2.8 |
| 40.12 g | 134.4 mg | 60637 | 2.6 |
| 40.80 g | 280.9 mg | 43733 | 2.6 |

EXAMPLE C22

Stock solution: methyl acrylate 48.66 g, ethyl acetate 191.74 g, AIBN 181.4 mg Polymerization 16 hour at 60° C.

| solution | compound 146 | Mn | PD |
|---|---|---|---|
| 40.0 g | 0 | 114382 | 3.9 |
| 38.76 g | 32.3 mg | 46884 | 1.6 |
| 38.68 g | 66.7 mg | 20071 | 1.6 |
| 37.07 g | 168.1 mg | 9990 | 1.4 |

EXAMPLE C23

Stock solution: methyl acrylate 81.28 g, ethyl acetate 320.34 g, AIBN 299.9 mg Polymerization 16 hour at 60° C.

| solution | compound | quantity | Mn | PD | $C_x$ |
|---|---|---|---|---|---|
| 39.22 g | — | 0 | 134884 | 3.4 | |
| 39.25 g | compound 121 | 256 mg | 10900 | 2 | 1.46 |
| 38.67 g | compound 122 | 251 mg | 12101 | 2.2 | 1.27 |
| 40.21 g | compound 123 | 331.7 mg | 20756 | 4.5 | 0.69 |
| 40.08 g | compound 125 | 233.6 mg | 16169 | 2.4 | 0.92 |
| 39.59 g | compound 119 | 218.8 mg | 7494 | 1.9 | 2.05 |
| 40.05 g | compound 120 | 256.3 mg | 12360 | 2.1 | 1.21 |
| 40.08 | compound 124 | 226.3 mg | 10905 | 2.1 | 1.3 |

D) APPLICATION EXAMPLES

Thermal Polymerization of Methyl Methacrylate
General Description of the Experiments.

The initial stock solution is separated in portions as listed below. After addition of various amounts of addition fragmentation agent, the magnetically stirred solutions are heated under inert atmosphere for a given period of time at a given temperature. After the reaction time the solutions are cooled in an ice bath and 25 ppm of stabilizer (hydroquinone) are added. The resulting reaction mixture is concentrated under reduced pressure and the polymer analyzed by GPC and NMR. To prevent any undesired reactions, solvents and monomers as well as reactants are purified by usual techniques before use.

EXAMPLE D1

Stock solution: methyl methacrylate 19.9 g, AIBN 33.2 mg; Polymerization 1 hour 60° C.; $C_x$ 0.73.

| solution | compound 119 | Mn | PD |
|---|---|---|---|
| 3.63 g | 0 | 248213 | 2.0 |
| 3.85 g | 36.7 mg | 39883 | 2.5 |
| 3.83 g | 88.0 mg | 17411 | 2.5 |
| 3.74 g | 176.3 mg | 11402 | 2.1 |

EXAMPLE D2

Stock solution: methyl methacrylate 60.5 g, AIBN 97 mg; Polymerization 1 hour 100° C.; $C_x$ 0.60.

| Solution | compound 119 | Mn | PD |
|---|---|---|---|
| 10.42 g | 0 | 146893 | 5.5 |
| 10.72 g | 47.2 mg | 55330 | 2.2 |

-continued

| Solution | compound 119 | Mn | PD |
|---|---|---|---|
| 10.04 g | 95.5 mg | 28977 | 1.9 |
| 10.01 g | 222.6 mg | 19445 | 1.9 |
| 10.33 g | 447.4 mg | 13683 | 1.9 |

EXAMPLE D3

Stock solution: methyl methacrylate 60.2 g, AIBN 99.5 mg; Polymerization 1 hour 60° C.; $C_x$ 0.27.

| Solution | compound 120 | Mn | PD |
|---|---|---|---|
| 10.52 g | 0 | 260800 | 1.7 |
| 9.86 g | 102.6 mg | 65500 | 1.8 |
| 9.80 g | 256.5 mg | 37661 | 1.5 |
| 10.15 g | 517.3 mg | 22343 | 1.7 |
| 10.28 g | 1034 mg | 14900 | 1.6 |

EXAMPLE D4

Stock solution: methyl methacrylate 60.6 g, AIBN 98.8 mg; Polymerization 1 hour 60° C.; $C_x$ 0.33.

| Solution | compound 124 | Mn | PD |
|---|---|---|---|
| 10.49 g | 0 | 230733 | 1.6 |
| 10.19 g | 103.7 mg | 51299 | 2.1 |
| 9.95 g | 234.7 mg | 34422 | 1.8 |
| 10.33 g | 456 mg | 23615 | 1.7 |
| 10.07 g | 918.7 mg | 12965 | 1.7 |

EXAMPLE D5

Stock solution: methyl methacrylate 61.1 g, AIBN 99.2 mg; Polymerization 1 hour 60° C.

| solution | compound | quantity | Mn | PD |
|---|---|---|---|---|
| 10.56 g | — | 0 | 184982 | 2.4 |
| 9.86 g | compound 121 | 279.7 mg | 8837 | 5.6 |
| 9.82 g | compound 122 | 270.4 mg | 25609 | 2.3 |
| 10.59 g | compound 123 | 360.8 mg | 32298 | 2.2 |
| 10.05 g | compound 125 | 244.2 mg | 27537 | 2.2 |

EXAMPLE D6

Stock solution: methyl methacrylate 98.1 g, AIBN 170.4 mg; Polymerization 1 hour 60° C.

| solution | compound 124 | Mn | PD |
|---|---|---|---|
| 10.02 g | 0 | 169431 | 2.5 |
| 9.94 g | 226.3 mg | 19189 | 2.3 |

EXAMPLE D7

Stock solution: methyl methacrylate 70.1 g, AIBN 112.7 mg; Polymerization 1 hour 60° C.

| solution | compound 129 | Mn | PD |
|---|---|---|---|
| 11.20 g | 0 | 209423 | 2.1 |
| 10.25 g | 295.6 mg | 173963 | 2.1 |

EXAMPLE D8

Stock solution: methyl methacrylate 70.1 g, AIBN 112.7 mg; Polymerization 1 hour 60° C.; $C_x$ 0.14.

| solution | compound 126 | Mn | PD |
|---|---|---|---|
| 11.20 g | 0 | 209423 | 2.1 |
| 10.08 g | 260.1 mg | 53962 | 3.7 |

EXAMPLE D9

Stock solution: methyl methacrylate 70.1 g, AIBN 112.7 mg; Polymerization 1 hour 60° C.; $C_x$ 0.46.

| solution | compound 130 | Mn | PD |
|---|---|---|---|
| 11.2 g | 0 | 209423 | 2.1 |
| 10.1 g | 301 mg | 19779 | 4.2 |

EXAMPLE D10

Stock solution: methyl methacrylate 50.4 g, AIBN 82.7 mg; Polymerization 1 hour 60° C.; $C_x$ 0.86.

| solution | compound 128 | Mn | PD |
|---|---|---|---|
| 9.75 g | 0 | 195555 | 2.0 |
| 10.59 g | 360.5 mg | 11371 | 1.9 |

EXAMPLE D11

Stock solution: methyl methacrylate 70.1 g, AIBN 112.7 mg; Polymerization 1 hour 60° C.; $C_x$ 0.47.

| solution | compound 131 | Mn | PD |
|---|---|---|---|
| 11.20 g | 0 | 209423 | 2.1 |
| 10.15 g | 547.6 mg | 19821 | 2.2 |

EXAMPLE D12

Stock solution: methyl methacrylate 60.5 g, AIBN 100.1 mg; Polymerization 1 hour 60° C.; $C_x$ 1.78.

| solution | compound 136 | Mn | PD |
|---|---|---|---|
| 9.09 g | 0 | 39478 | 4.4 |
| 10.6 g | 142.5 mg | 11130 | 2.9 |

EXAMPLE D13

Stock solution: methyl methacrylate 60.5 g, AIBN 100.1 mg; Polymerization 1 hour 60° C.; $C_x$ 0.12.

| solution | compound 133 | Mn | PD |
|---|---|---|---|
| 9.68 g | 0 | 75937 | 2.6 |
| 10.60 g | 161.4 mg | 52081 | 2.6 |
| 11.29 g | 405 mg | 32355 | 2.5 |

EXAMPLE D14

Stock solution: methyl methacrylate 59.8 g, AIBN 99.9 mg; Polymerization 1 hour 60° C.; $C_x$ 0.24.

| solution | compound 134 | Mn | PD |
|---|---|---|---|
| 9.09 g | 0 | 39478 | 4.4 |
| 5.69 g | 78.2 mg | 27635 | 2.1 |

EXAMPLE D15

Stock solution: methyl methacrylate 59.8 g, AIBN 99.9 mg; Polymerization 1 hour 60° C.; $C_x$ 0.21.

| solution | compound 135 | Mn | PD |
|---|---|---|---|
| 9.09 g | 0 | 39478 | 4.4 |
| 10.26 g | 173.4 mg | 27666 | 2.4 |

EXAMPLE D16

Stock solution: methyl methacrylate 60.7 g, AIBN 101.9 mg; Polymerization 1 hour 60° C.; $C_x$ 0.90.

| solution | compound 102 | Mn | PD |
|---|---|---|---|
| 10.37 g | 0 | 225272 | 2.1 |
| 12.53 g | 121.5 mg | 16629 | 2.3 |
| 9.13 g | 208.3 mg | 9211 | 2.0 |
| 9.42 g | 325.3 mg | 7613 | 2.0 |
| 9.51 g | 944.3 mg | 3771 | 2.0 |

EXAMPLE D17

Stock solution: methyl methacrylate 61.0 g, AIBN 98.6 mg; Polymerization 1 hour 60° C.

| solution | compound 112 | Mn | PD |
|---|---|---|---|
| 9.85 g | 0 | 193862 | 2.2 |
| 6.94 g | 33.2 mg | 78406 | 3.3 |
| 10.09 g | 95.8 mg | 51526 | 4.4 |
| 5.02 g | 244.1 mg | 45745 | 2.2 |

EXAMPLE D18

Stock solution: methyl methacrylate 60.2 g, AIBN 98.8 mg; Polymerization 1 hour 60° C.; $C_x$ 0.72.

| solution | compound 139 | Mn | PD |
|---|---|---|---|
| 9.80 g | 0 | 171059 | 2.2 |
| 6.07 g | 29.50 mg | 43723 | 3.2 |
| 11.35 g | 123.7 mg | 30824 | 3.1 |
| 10.35 g | 287.1 mg | 25155 | 3.6 |
| 7.12 g | 339.5 mg | 11411 | 2.8 |

EXAMPLE D19

Stock solution: methyl methacrylate 59.3 g, AIBN 99.4 mg; Polymerization 1 hour 60° C.; $C_x$ 0.41.

| solution | compound 138 | Mn | PD |
|---|---|---|---|
| 9.59 g | 0 | 205250 | 2.3 |
| 9.91 g | 21.8 mg | 108582 | 2.4 |
| 10.20 g | 303 mg | 28953 | 2.1 |
| 10.06 g | 436.7 mg | 21155 | 2.1 |

EXAMPLE D20

Stock solution: methyl methacrylate 62.3 g, AIBN 103.1 mg; Polymerization 1 hour 60° C.; $C_x$ 0.58.

| solution | compound 103 | Mn | PD |
|---|---|---|---|
| 9.22 g | 0 | 215653 | 1.9 |
| 9.90 g | 99.4 mg | 28888 | 4.9 |
| 9.82 g | 185.7 mg | 16155 | 7.2 |
| 9.84 g | 406 mg | 11846 | 5.1 |

EXAMPLE D21

Stock solution: methyl methacrylate 60.8 g, AIBN 98.4 mg; Polymerization 1 hour 60° C.

| solution | compound 143 | Mn | PD |
|---|---|---|---|
| 9.59 g | 0 | 249832 | 2.1 |
| 7.98 g | 57.2 mg | 26815 | 3.7 |
| 7.76 g | 142.5 mg | 10898 | 5.3 |

EXAMPLE D22

Stock solution: methyl acrylate 57.6 g, MEK 59.8 g, AIBN 101.0 mg; Polymerization 1 hour 60° C.; $C_x$ 0.25.

| solution | compound 141 | Mn | PD |
|---|---|---|---|
| 18.51 g | 0 | 123834 | 2.1 |
| 19.44 g | 34.7 mg | 130013 | 2.7 |
| 19.19 g | 73.6 mg | 43228 | 2.1 |
| 19.47 g | 167.2 mg | 51257 | 1.5 |
| 18.27 g | 341.6 mg | 23847 | 1.5 |

EXAMPLE D23

Stock solution: methyl methacrylate 70.1 g, AIBN 112.7 mg; Polymerization 1 hour 60° C.

| solution | compound 145 | Mn | PD |
|---|---|---|---|
| 11.2 g | 0 | 209423 | 2.1 |
| 10.1 g | 275 mg | 75781 | 3.5 |

EXAMPLE D24

Stock solution: methyl methacrylate 62.3 g, AIBN 215.4 mg; Polymerization 1 hour 60° C.

| solution | compound 146 | Mn | PD |
|---|---|---|---|
| 9.58 g | 0 | 137396 | 2.1 |
| 10.13 g | 33.1 mg | 113786 | 2.2 |
| 10.12 g | 172.5 mg | 73878 | 2.5 |
| 10.10 g | 336.2 mg | 40488 | 3.6 |

EXAMPLE D25

Stock solution: methyl methacrylate 60.0 g, AIBN 100 mg; Polymerization 1 hour 60° C.

| solution | compound 148 | Mn | PD |
|---|---|---|---|
| 9.73 g | 0 | 179929 | 2.1 |
| 9.76 g | 43.7 mg | 85792 | 3.2 |
| 7.86 g | 129 mg | 22126 | 4.3 |
| 7.39 g | 270.4 mg | 16898 | 4.3 |

EXAMPLE D26

Stock solution: methyl methacrylate 60.0 g, AIBN 97.8 mg; Polymerization 1 hour 60° C.

| solution | compound 110 | Mn | PD |
|---|---|---|---|
| 10.54 g | 0 | 195958 | 3.1 |
| 9.79 g | 44.2 mg | 130013 | 2.7 |
| 10.34 g | 93.1 mg | 89698 | 2.6 |
| 10.30 g | 182.3 mg | 23198 | 4.9 |
| 10.94 g | 672.2 mg | 14983 | 3.8 |

EXAMPLE D27

Stock solution: methyl methacrylate 60.0 g, AIBN 99.0 mg; Polymerization 1 hour 60° C.; $C_x$ 0.22.

| solution | compound 109 | Mn | PD |
|---|---|---|---|
| 9.30 g | 0 | 230238 | 1.8 |
| 10.55 g | 105.3 mg | 125748 | 1.8 |
| 10.48 g | 204.7 mg | 81490 | 1.7 |
| 10.68 g | 588.5 mg | 47372 | 1.7 |
| 10.79 g | 962.0 mg | 22797 | 1.7 |

EXAMPLE D28

Stock solution: methyl methacrylate 61.4 g, AIBN 99.4 mg; Polymerization 1 hour 60° C.

| solution | compound 116 | Mn | PD |
|---|---|---|---|
| 10.48 g | 0 | 118726 | 3.9 |
| 9.88 g | 134.5 mg | 3553 | 1.6 |

EXAMPLE D29

Stock solution: methyl methacrylate 59.9 g, MEK 59.64 g, AIBN 97.8 mg; Polymerization 1 hour 60° C.

| solution | compound | quantity | Mn | PD |
|---|---|---|---|---|
| 21.64 g | — | 0 | 125296 | 2.3 |
| 19.82 g | compound 156 | 390.8 mg | 56049 | 2.2 |
| 20.04 g | compound 157 | 412.9 mg | 49724 | 1.9 |

EXAMPLE D30

Stock solution: methyl methacrylate 59.8 g, AIBN 99.9 mg; Polymerization 1 hour 60° C.; $C_x$ 2.49.

| solution | compound 161 | Mn | PD |
|---|---|---|---|
| 8.97 g | 0 | 146007 | 2.5 |
| 9.68 g | 34.5 mg | 17881 | 3.0 |
| 9.97 g | 66.4 mg | 9077 | 3.0 |
| 10.01 g | 336.1 mg | 3529 | 2.2 |

E) APPLICATION EXAMPLES

Thermal Polymerization of Styrene
General Description of the Experiments.

The initial stock solution is separated in portions as listed below. After addition of various amounts of addition fragmentation agent, the magnetically stirred solutions are heated under inert atmosphere for a given period of time at a given temperature. After the reaction time the solutions are cooled in an ice bath and 25 ppm of stabilizer (hydroquinone) are added. The resulting reaction mixture is concentrated under reduced pressure and the polymer analyzed by GPC and NMR. To prevent any undesired reactions, solvents and monomers as well as reactants are purified by usual techniques before use.

EXAMPLE E1

Stock solution: styrene 105.0 g, AIBN 159.6 mg; Polymerization 2 hours 80° C.

| solution | compound | quantity | Mn | PD |
|---|---|---|---|---|
| 10.60 g | — | 0 | 57784 | 1.7 |
| 9.40 g | compound 121 | 267.3 mg | 18915 | 2.0 |
| 9.84 g | compound 122 | 267.6 mg | 22027 | 2.1 |
| 9.91 g | compound 123 | 337.3 mg | 25770 | 2.2 |
| 9.86 g | compound 125 | 242.1 mg | 18356 | 2.2 |

EXAMPLE E2

Stock solution: styrene 70.9 g, AIBN 108.7 mg; Polymerization 2 hours 80° C.

| solution | compound 126 | Mn | PD |
|---|---|---|---|
| 9.10 g | 0 | 53221 | 1.8 |
| 10.29 g | 245 mg | 45551 | 1.9 |

EXAMPLE E3

Stock solution: styrene 70.9 g, AIBN 108.7 mg; Polymerization 2 hours 80° C.

| solution | compound 130 | Mn | PD |
|---|---|---|---|
| 9.10 g | 0 | 53221 | 1.8 |
| 9.95 g | 283.4 mg | 33795 | 1.9 |

EXAMPLE E4

Stock solution: styrene 70.9 g, AIBN 108.7 mg; Polymerization 2 hours 80° C.

| solution | compound 119 | Mn | PD |
|---|---|---|---|
| 9.10 g | 0 | 53221 | 1.8 |
| 10.25 g | 437.4 mg | 14259 | 2.1 |

EXAMPLE E5

Stock solution: styrene 70.9 g, AIBN 108.7 mg; Polymerization 2 hours 80° C.

| solution | compound 128 | Mn | PD |
|---|---|---|---|
| 9.10 g | 0 | 53221 | 1.8 |
| 9.82 g | 348.6 mg | 12842 | 2.1 |

EXAMPLE E6

Stock solution: styrene 61.7 g, AIBN 95.2 mg; Polymerization 2 hours 80° C.

| solution | compound 136 | Mn | PD |
|---|---|---|---|
| 9.03 g | 0 | 49018 | 1.9 |
| 4.87 g | 645 mg | 16837 | 2.2 |

EXAMPLE E7

Stock solution: styrene 61.7 g, AIBN 95.2 mg; Polymerization 2 hours 80° C.

| solution | compound 133 | Mn | PD |
|---|---|---|---|
| 9.03 g | 0 | 49018 | 1.9 |
| 9.54 g | 125.9 mg | 32942 | 2.0 |

EXAMPLE E8

Stock solution: styrene 61.7 g, AIBN 87.5 mg; Polymerization 2 hours 80° C.

| solution | compound 134 | Mn | PD |
|---|---|---|---|
| 9.95 g | 0 | 54190 | 1.8 |
| 5.21 g | 67.0 mg | 22453 | 2.1 |
| 3.45 g | 90.7 mg | 19233 | 2.2 |

EXAMPLE E9

Stock solution: styrene 61.7 g, AIBN 87.5 mg; Polymerization 2 hours 80° C.

| solution | compound 135 | Mn | PD |
|---|---|---|---|
| 9.95 g | 0 | 54190 | 1.8 |
| 10.02 g | 143.0 mg | 19358 | 2.0 |
| 5.00 g | 171.1 mg | 15679 | 2.2 |

EXAMPLE E10

Stock solution: styrene 70.9 g, AIBN 108.7 mg; Polymerization 2 hours 80° C.

| solution | compound 145 | Mn | PD |
|---|---|---|---|
| 9.10 g | 0 | 53221 | 1.8 |
| 10.18 g | 275.9 mg | 43328 | 2.0 |

EXAMPLE E11

Stock solution: styrene 59.7 g, AIBN 98 mg; Polymerization 2 hours 80° C.

| solution | compound 155 | Mn | PD |
|---|---|---|---|
| 9.13 g | 0 | 46783 | 1.9 |
| 9.96 g | 54.4 mg | 25429 | 2.3 |
| 9.50 g | 110.5 mg | 17226 | 2.6 |
| 9.47 g | 256.6 mg | 8086 | 3.5 |
| 9.77 g | 551.5 mg | 5293 | 3.4 |

EXAMPLE E12

Stock solution: styrene 60.9 g, heptane 60.9 g, AIBN 101.8 mg; Polymerization 2 hours 80° C.

| solution | compound 157 | Mn | PD |
|---|---|---|---|
| 16.84 g | 0 | 32501 | 1.7 |
| 19.39 g | 223.4 mg | 24770 | 1.7 |
| 21.24 g | 422.8 mg | 18650 | 1.7 |

EXAMPLE E13

Stock solution: styrene 65.2 g, AIBN 186 mg; Polymerization 2 hours 80° C.

| solution | compound 161 | Mn | PD |
|---|---|---|---|
| 9.11 g | 0 | 48277 | 1.9 |
| 10.26 g | 39.6 mg | 11105 | 3.9 |
| 9.68 g | 69.2 mg | 7745 | 4.0 |
| 10.08 g | 168.0 mg | 6857 | 4.1 |

F) APPLICATION EXAMPLES

Thermal Polymerization of n-Butyl Acrylate

General Description of the Experiments.

The initial stock solution is separated in portions as listed below. After addition of various amounts of addition fragmentation agent, the magnetically stirred solutions are heated under inert atmosphere for a given period of time at a given temperature. After the reaction time the solutions are cooled in an ice bath and 25 ppm of stabilizer (hydroquinone) are added. The resulting reaction mixture is concentrated under reduced pressure, further dried under high vacuum, and the polymer analyzed by GPC and NMR. To prevent any undesired reactions, solvents and monomers as well as reactants are purified by usual techniques before use.

EXAMPLE F1

Stock solution: n-butyl acrylate 53.97 g, toluene 125.9 g, AIBN 139.8 mg; Polymerization 16 hours 60° C.; $C_x$ 0.7.

| solution | compound 119 | Mn | PD |
|---|---|---|---|
| 30.1 g | 0 | 45943 | 3.8 |
| 29.7 g | 63.8 mg | 22308 | 2.5 |
| 30.1 g | 159.1 mg | 13680 | 2.2 |
| 29.8 g | 319.2 mg | 10113 | 2.0 |
| 30.0 g | 636.9 mg | 7026 | 2.0 |

EXAMPLE F2

Stock solution: n-butyl acrylate 102.1 g, toluene 238.2 g, AIBN 262.5 mg; Polymerization 16 hours 60° C.; $C_x$ 1.1.

| solution | compound 120 | Mn | PD |
|---|---|---|---|
| 20.6 g | 0 | 53095 | 3.9 |
| 20.5 g | 49.9 mg | 48003 | 2.5 |
| 20.0 g | 122.2 mg | 31013 | 2.3 |
| 20.0 g | 243.7 mg | 16210 | 2.2 |
| 19.8 g | 484.1 mg | 5735 | 2.2 |

EXAMPLE F3

Stock solution: n-butyl acrylate 54.0 g, toluene 126.0 g, AIBN 139.5 mg; Polymerization 16 hours 60° C.; $C_x$ 1.1.

| solution | compound 128 | Mn | PD |
|---|---|---|---|
| 29.6 g | 0 | 37627 | 5.0 |
| 29.4 g | 50.1 mg | 21055 | 2.1 |
| 29.4 g | 126.6 mg | 12250 | 2.1 |
| 29.5 g | 250.2 mg | 7627 | 1.9 |
| 29.9 g | 497.9 mg | 5031 | 1.8 |

EXAMPLE F4

Stock solution: n-butyl acrylate 102.2 g, toluene 238.5 g, AIBN 261.6 mg; Polymerization 16 hours 60° C.; $C_x$ 2.8.

| solution | compound 150 | Mn | PD |
|---|---|---|---|
| 30.5 g | 0 | 49064 | 3.6 |
| 30.6 g | 80.3 mg | 19818 | 2.2 |
| 30.9 g | 180.5 mg | 7808 | 2.0 |
| 30.7 g | 362.2 mg | 4450 | 1.7 |

EXAMPLE F5

Stock solution: n-butyl acrylate 108.2 g, toluene 251.1 g, AIBN 278.4 mg; Polymerization 16 hours 60° C.; $C_x$ 1.8.

| solution | compound 151 | Mn | PD |
|---|---|---|---|
| 30.6 g | 0 | 47194 | 3.8 |
| 29.8 g | 59.9 mg | 19454 | 2.0 |
| 30.2 g | 150.7 mg | 8913 | 1.8 |
| 30.1 g | 299.8 mg | 5500 | 1.7 |
| 29.4 g | 599.8 mg | 3187 | 1.7 |

EXAMPLE F6

Stock solution: n-butyl acrylate 54.1 g, toluene 126.0 g, AIBN 141.6 mg; Polymerization 16 hours 60° C.; $C_x$ 1.1.

| solution | compound 152 | Mn | PD |
|---|---|---|---|
| 29.8 g | 0 | 36417 | 4.6 |
| 30.3 g | 73.2 mg | 18243 | 2.2 |
| 30.5 g | 159.3 mg | 12324 | 2.2 |
| 30.3 g | 344.3 mg | 8557 | 2.0 |
| 30.8 g | 655.4 mg | 4822 | 2.1 |

EXAMPLE F7

Stock solution: n-butyl acrylate 54.2 g, toluene 126.4 g, AIBN 138.7 mg; Polymerization 16 hours 60° C.; $C_x$ 2.1.

| solution | compound 153 | Mn | PD |
|---|---|---|---|
| 30.0 g | 0 | 64228 | 2.8 |
| 30.3 g | 72.6 mg | 21700 | 2.0 |
| 30.5 g | 177.1 mg | 9721 | 2.1 |
| 30.5 g | 351.7 mg | 5783 | 1.9 |

What is claimed is:

1. A composition comprising
   a) at least one ethylenically unsaturated monomer or oligomer
   b) a radical initiator which forms a radical upon heating or upon irradiation with (UV) light from 305 nm to 450 nm and
   c) a compound of formula (Ia), (Ib) or (Ic)

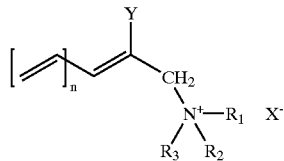
(Ia)

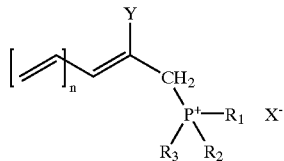
(Ib)

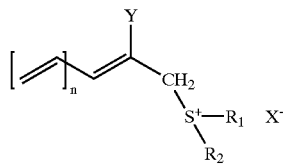
(Ic)

wherein

Y is a group which activates the double bond towards Michael addition;

X is halogen or the anion of a mono carboxylic acid from 1–12 carbon atoms, a monovalent oxo acid or complex acid;

n is 0 or 1;

$R_1$, $R_2$ $R_3$ are independently of each other hydrogen, unsubstituted $C_1$–$C_{18}$alkyl, $C_3$–$C_{18}$alkyl, interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl or $C_3$–$C_{18}$alkyl interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino, $C_1$–$C_4$alkylamino, di($C_1$–$C_4$alkyl)amino or by a group —O—C(O)—$C_1$–$C_8$alkyl; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or $R_1$ and $R_2$, together with the linking hetero atom, form a $C_3$–$C_{12}$ heterocycloalkyl radical; or $R_1$ and $R_2$ form a group

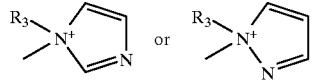

or
R₁, R₂ and R₃ form a group

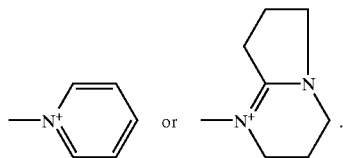

2. A composition according to claim 1, wherein Y is CN, C(O)halogen, COOR₄, C(O)R₄, CONR₅R₆, phenyl or naphthyl which are unsubstituted or substituted by C₁–C₄alkyl, C₁–C₄alkoxy, C₁–C₄alkylthio, halogen, nitro, cyano, hydroxy, carboxy, C₁–C₄alkylamino or di(C₁–C₄alkyl) amino; and R₄, R₅ and R₆ are hydrogen or C₁–C₁₈alkyl.

3. A composition according to claim 2, wherein Y is CN, COOR₄ or phenyl which is unsubstituted or substituted by C₁–C₄alkyl, C₁–C₄alkoxy, C₁–C₄alkylthio, halogen, cyano, hydroxy, carboxy, C₁–C₄alkylamino or di(C₁–C₄alkyl) amino; and R₄ is C₁–C₄alkyl.

4. A composition according to claim 1, wherein X is Cl⁻, Br⁻, I⁻, ClO₄⁻, CF₃SO₃⁻, CH₃SO₃⁻, CF₃COO⁻, p-toluene sulfonate, HSO₄⁻, BF₄⁻, B(Phenyl)₄⁻, PF₆⁻, SbCl₆⁻, AsF₆⁻, SbF₆⁻ or a mono carboxylic acid from 1–12 carbon atoms.

5. A composition according to claim 4, wherein X is Cl⁻, Br⁻, ClO₄⁻, CF₃SO₃⁻, CH₃SO₃⁻, CF₃COO⁻, BF₄⁻, or PF₆⁻.

6. A composition according to claim 1, wherein n is 0.

7. A composition according to claim 1, wherein R₁, R₂ and R₃ are independently of each other unsubstituted C₁–C₁₈alkyl, C₃–C₁₈alkyl interrupted by at least one nitrogen or oxygen atom, C₇–C₉phenylalkyl, C₃–C₁₂cycloalkyl or C₃–C₁₂cycloalkyl containing at least one nitrogen or oxygen atom; or C₁–C₁₈alkyl, C₃–C₁₈alkyl interrupted by at least one nitrogen or oxygen atom, C₇–C₉phenylalkyl, C₃–C₁₂cycloalkyl or C₃–C₁₂cycloalkyl containing at least one nitrogen or oxygen atom, which are substituted by NO₂, halogen, amino, hydroxy, cyano, carboxy, C₁–C₄alkoxy, C₁–C₄alkylthio, C₁–C₄alkylamino or di(C₁–C₄alkyl)amino; or phenyl, which is unsubstituted or substituted by C₁–C₄alkyl, C₁–C₄alkoxy, C₁–C₄alkylthio, halogen, cyano, hydroxy, carboxy, C₁–C₄alkylamino or di(C₁–C₄alkyl) amino; or R₁ and R₂, together with the linking hetero atom, form a C₄–C₇ heterocycloalkyl radical; or R₁ and R₂ form a group

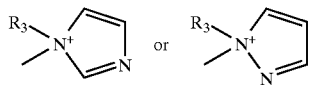

or R₁, R₂ and R₃ form a group

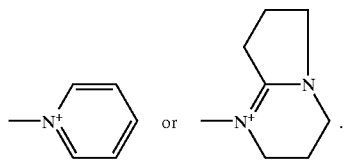

8. A composition according to claim 7, wherein R₁, R₂ and R₃ independently of each other are unsubstituted C₁–C₁₂alkyl, C₃–C₁₂alkyl interrupted by at least one nitrogen or oxygen atom, benzyl or phenyl, which is unsubstituted or substituted by C₁–C₄alkyl, C₁–C₄alkoxy, C₁–C₄alkylthio, halogen, cyano, hydroxy, carboxy.

9. A composition according to claim 1, wherein Y is CN, C(O)halogen, COOR₄, phenyl which is unsubstituted or substituted by C₁–C₄alkyl, C₁–C₄alkoxy, C₁–C₄alkylthio, halogen, cyano, hydroxy, carboxy, R₄, is C₁–C₈alkyl; X is Br⁻, ClO₄⁻, CF₃SO₃⁻, CH₃SO₃⁻, CF₃COO⁻, BF₄⁻ or PF₆⁻; and R₁, R₂ and R₃ independently of each other are unsubstituted C₁–C₁₂alkyl, C₃–C₁₂alkyl interrupted by at least one nitrogen or oxygen atom, benzyl or phenyl, which is unsubstituted or substituted by C₁–C₄alkyl, C₁–C₄alkoxy, C₁–C₄alkylthio, halogen, cyano, hydroxy, carboxy.

10. A composition according to claim 1, wherein the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides and vinylidene halides.

11. A composition according to claim 10 wherein the ethylenically unsaturated monomer is ethylene, propylene, n-butylene, i-butylene, isoprene, 1,3-butadiene, α-C₅–C₁₈alkene, styrene, α-methyl styrene, p-methyl styrene or a compound of formula $CH_2=C(R_a)-(C=Z)-R_b$, wherein $R_a$ is hydrogen or C₁–C₄alkyl, $R_b$ is NH₂, O⁻(Me⁺), glycidyl, unsubstituted C₁–C₁₈alkoxy, C₂–C₁₀₀alkoxy interrupted by at least one N and/or O atom, or hydroxy-substituted C₁–C₁₈alkoxy, unsubstituted C₁–C₁₈alkylamino, di(C₁–C₁₈alkyl)amino, hydroxy-substituted C₁–C₁₈alkylamino or hydroxy-substituted di(C₁–C₁₈alkyl) amino, —O—CH₂—CH₂—N(CH₃)₂ or —O—CH₂—CH₂—N⁺H(CH₃)₂ An⁻; An⁻ is a anion of a monovalent organic or inorganic acid; Me is a monovalent metal atom or the ammonium ion, Z is oxygen or sulfur.

12. A composition according to claim 11, wherein $R_a$ is hydrogen or methyl, $R_b$ is NH₂, gycidyl, unsubstituted or with hydroxy substituted C₁–C₄alkoxy, unsubstituted C₁–C₄alkylamino, di(C₁–C₄alkyl)amino, hydroxy-substituted C₁–C₄alkylamino or hydroxy-substituted di(C₁–C₄alkyl)amino; and Z is oxygen.

13. A composition according to claim 11 in which the ethylenically unsaturated monomers are selected from the group consisting of styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth) acrylates, acrylonitrile, acrylamide, methacrylamide and dimethylaminopropyl-methacrylamide.

14. A process for preparing an oligomer, a cooligomer, a polymer or a copolymer (block or random) by free radical polymerization of
   a) at least one ethylenically unsaturated monomer or oligomer, which comprises (co)polymerizing the monomer or monomers/oligomers in the presence of
   b) a radical initiator which forms a radical upon heating or upon irradiation with (UV) light from 305 nm to 450 nm and
   c) a compound of formula (Ia), (Ib) or (Ic) according to claim 1 by subjecting the mixture to heat or electromagnetic radiation in the wavelength range from 305 nm to 450 nm.

15. A process according to claim 14, wherein the radical initiator b) is present in an amount of 0.01 to 5 mol % based on the monomer or monomer mixture.

16. A process according to claim 14, wherein the compound of formula (Ia), (Ib) or (Ic) is present in an amount of 0.01 to 10 mol % based on the monomer or monomer mixture.

17. A polymer or copolymer prepared by the process of claim 14 containing a vinyl- or 1,3 dienyl group at one end of the molecule.

18. A compound of formula (Ia), (Ib) or (Ic)

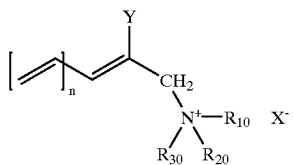 (Ia)

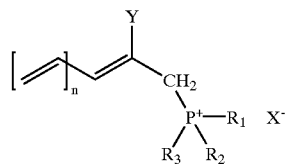 (Ib)

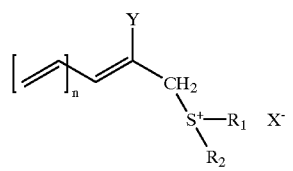 (Ic)

wherein

Y is CN, C(O)halogen, $COOR_4$, $C(O)R_4$, $CONR_5R_6$, phenyl or naphthyl which are unsubstituted or substituted by $C_1$–$C_4$alkyl, $C_1$–$C_4$alkoxy, $C_1$–$C_4$alkylthio, halogen, nitro, cyano, hydroxy, carboxy, $C_1$–$C_4$alkylamino or di($C_1$–$C_4$alkyl)amino; and $R_4$, $R_5$ and $R_6$ are hydrogen or $C_1$–$C_{18}$alkyl;

X is $Cl^-$, $Br^-$, $—I^-$, $ClO_4^-$, $CF_3SO_3^-$, $CH_3SO_3^-$, $CF_3COO^-$, p-toluene sulfonate, $HSO_4^-$, $BF_4^-$, $B(Phenyl)_4^-$, $PF_6^-$, $SbCl_6^-$, $AsF_6^-$, $SbF_6^-$ or a mono carboxylic acid from 1–12 carbon atoms;

n is 0 or 1;

$R_1$, $R_2$ $R_3$ are independently of each other hydrogen, unsubstituted $C_1$–$C_{18}$alkyl, $C_3$–$C_{18}$alkyl, interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_3$–$C_{18}$alkyl, interrupted by at least one nitrogen or oxygen atom, $C_3$–$C_{18}$alkenyl, $C_3$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino, di($C_1$–$C_4$alkyl)amino or by a group —O—C(O)—$C_1$–$C_{18}$alkyl; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or $R_1$ and $R_2$, together with the linking hetero atom, form a $C_3$–$C_{12}$heterocycloalkyl radical;

$R_{10}$ and $R_{20}$ are independently of each other $C_3$–$C_{18}$alkyl which is unsubstituted or substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; and $R_{30}$ is hydrogen or methyl.

19. A compound of formula (Ia) according to claim 18, wherein Y is phenyl, CN or $COOR_4$ and $R_4$ is $C_1$–$C_4$alkyl.

20. A compound of formula (Ia) according to claim 18, wherein X is Cl or Br.

* * * * *